(12) United States Patent
Sergeeva et al.

(10) Patent No.: US 7,163,923 B2
(45) Date of Patent: Jan. 16, 2007

(54) PEPTIDE DEFORMYLASE ACTIVATED PRODRUGS

(75) Inventors: Maria V. Sergeeva, San Diego, CA (US); Venkata Ramana Doppalapudi, San Diego, CA (US)

(73) Assignee: Celmed Oncology (USA), Inc., Saint-Laurent (CA)

( * ) Notice: Subject to any disclaimer, the term of this patent is extended or adjusted under 35 U.S.C. 154(b) by 328 days.

(21) Appl. No.: 10/142,089

(22) Filed: May 9, 2002

(65) Prior Publication Data

US 2003/0091587 A1    May 15, 2003

Related U.S. Application Data

(60) Provisional application No. 60/290,099, filed on May 9, 2001.

(51) Int. Cl.
    C07K 5/06    (2006.01)
(52) U.S. Cl. .......................... 514/19; 514/18; 530/331
(58) Field of Classification Search .................. 514/2, 514/18, 19; 530/331
    See application file for complete search history.

(56) References Cited

U.S. PATENT DOCUMENTS

| | | | | | |
|---|---|---|---|---|---|
| 4,053,638 | A | * | 10/1977 | Litchfield et al. ............. | 514/54 |
| 4,071,511 | A | * | 1/1978 | Takemoto et al. ........... | 530/335 |
| 4,083,974 | A | * | 4/1978 | Turi ............................ | 514/174 |
| 4,339,440 | A | | 7/1982 | Gjerløv | |
| 4,415,590 | A | * | 11/1983 | Gerzon ........................ | 514/561 |
| 4,427,660 | A | * | 1/1984 | Schiffman et al. ............ | 514/18 |
| 5,274,113 | A | * | 12/1993 | Kang et al. .................. | 548/405 |
| 5,350,681 | A | * | 9/1994 | Iacobucci et al. ........... | 435/68.1 |
| 5,918,568 | A | * | 7/1999 | Gjerl.o slashed.v ......... | 119/650 |
| 6,110,908 | A | * | 8/2000 | Guthery ...................... | 514/188 |
| 6,143,790 | A | * | 11/2000 | Hallinan et al. ............. | 514/631 |
| 6,159,706 | A | | 12/2000 | Shepard ........................ | 435/32 |
| 6,245,750 | B1 | | 6/2001 | Shepard ........................ | 514/51 |
| 6,339,151 | B1 | | 1/2002 | Shepard et al. ............ | 536/26.8 |
| 6,448,058 | B1 | | 9/2002 | Patel et al. | |
| 6,613,879 | B1 | * | 9/2003 | Firestone et al. ........... | 530/330 |

FOREIGN PATENT DOCUMENTS

| WO | WO 98/13059 A | 4/1998 |
|---|---|---|
| WO | WO 99/08110 | 2/1999 |
| WO | WO 99/37753 | 7/1999 |
| WO | WO 01/07454 A1 | 2/2001 |
| WO | WO 03/088913 A2 | 10/2003 |
| WO | WO 2004/43400 A2 | 5/2004 |

OTHER PUBLICATIONS

Apfel, C. et al. "Hydroxamic acid derivatives as potent peptide deformylase inhibitors and antibacterial agents" J. Med. Chem. (2000) 43:2324-2331.

Apfel, C.M. et al. "Peptide deformylase as an antibacterial drug target: Assays for detection of its inhibition in *Escherichia coli* cell homogenates and intact cells" Anti. Agents and Chemo. (Apr. 2001a) 45(4):1053-1057.

Apfel, C.M. et al. "Peptide deformylase as an antibacterial drug target: Target validation and resistance development" Anti. Agents and Chemo. (Apr. 2001b) 45(4):1058-1064.

Becker, A. et al. "Iron center, substrate recognition and mechanism of peptide deformylase" Nat. Struct. Biol. (Dec. 1998) 5(12):1053-1058.

Chan, M. K. et al. "Crystal structure of the *Escherichia coli* peptide deformylase" Biochem. (1997) 36:13904 13909.

Chen D.Z. et al. "Actinonin, a naturally occurring antibacterial agent, is a potent deformylase inhibitor" Biochem. (2000) 39(6):1256-1262.

Clements, J.M. et al. "Antibiotic activity and characterization of BB-3497, a novel peptide deformylase inhibitor" Anti. Agents and Chemo. (Feb. 2001) 45(2):563-570.

de Groot, F.M.H. et al. "Synthesis and biological evaluation of 2'-carbamate-linked and 2'-carbonate-linked prodrugs of paclitaxel: selective activation by the tumor-associated protease plasmin" J. Med. Chem. (2000) 43:3093-3102.

Durand, D.J. et al. "Peptide aldehyde inhibitors of bacterial peptide deformylases" Arch. Biochem. & Biophysics. (Jul 15, 1999) 367(2): 297-302.

Giglione, C. et al. "Peptide deformylase as a target for new generation, broad spectrum antimicrobial agents" Mol. Microbiol. (2000a) 36(6):1197-1205.

Giglione, C. et al. "Identification of eukaryotic peptide deformylases reveals universality of N-terminal protein processing mechanisms" EMBO J. (2000b) 19(21):5916-5929.

Hao, B. et al. "Structural basis for the design of antibiotics targeting peptide deformylase" Biochem. (1999) 38(15):4712-4719.

Hu, Y.J. et al. "H-phosphonate derivatives as novel peptide deformylase inhibitors" Bioorg Med Chem Letts. (1998) 8(18):2479-2482.

Huntington, K.M. et al. "Synthesis and antibacterial activity of peptide deformylase inhibitors" Biochem. (2000) 39(15):4543-4551.

Jayasekera, M.M.K. et al. "Novel nonpeptidic inhibitors of peptide deformylase" Arch. Biochem. & Biophys. (Sep. 15, 2000) 381(2):313-316.

Meinnel, T. et al. "Methionine as translation start signal: A review of the enzymes of the pathway in *Escherichia coli*" Biochimie. (1993) 75(12):1061-1075.

(Continued)

*Primary Examiner*—David Lukton
(74) *Attorney, Agent, or Firm*—Foley & Lardner LLP

(57) ABSTRACT

This invention provides a method for inhibiting the growth of a microorganism that expresses Peptide Deformylase by contacting the microorganism with an effective amount of the compound described herein. This method inhibits the growth of gram-positive and gram-negative microorganism, e.g., *S. aureus, S. epidermidis, K. pneumoniae, E. aerogenes, E. cloacae, M. catarrhalis, E. coli, E. faecalis, H. influenzae* and *P. aeruginosa*. This method can be practiced in vitro, ex vivo and in vivo. Further provided is a method for alleviating the symptoms of an infection by a Peptide Deformylase expressing microorganism in a subject by administering or delivering to the subject an effective amount of the compound described above.

23 Claims, 5 Drawing Sheets

OTHER PUBLICATIONS

Ragusa S., et al. "Control of peptide deformylase activity by metal cations" *J.Mol.Biol.* (1998) 280:515-523.

Rajagopalan, P.T.R. et al. "Purification, characterization, and inhibition of peptide deformylase from *Escherichia coli*" *Biochem.* (1997) 36(45):13910-13918.

Rajagopalan, P.T.R. et al. "Oxygen-mediated inactivation of peptide deformylase" *J. Biol. Chem.* (Aug. 28, 1998) 273(35):22305-22310.

Wei Y. and D. Pei "Continuous spectrophotometric assay of peptide deformylase" *Anal Biochem.* (1997) 250(1):29-34.

Wei, Y. et al. "Identification of a potent peptide deformylase inhibitor from a rationally designed combinatorial library" *J Comb Chem.* (2000) 2(6):650-657.

Wei, Y. and D. Pei "Activation of antibacterial prodrugs by peptide deformylase" *Bioorg Med Chem Letts.* (2000b) 10(10):1073-1078.

Lackey, D.B et al. "Enzyme-Catalyzed Therapeutic Agent (ECTA) Design: Activation of the Antitumor ECTA Compound NB 1011 by Thymidylate Synthase" *Biochem Pharm.* (2001) 61:179-189.

Dubowchick, G.M. et al. "Cathepsin B-Sensitive Dipeptide Prodrugs. 1. A Model Study of Structural Requirements for Efficient Release of Doxorubicin" *Bioorg. & Med. Chem Letters* (1998) 8(23):3341-3346.

de Groot, F.M.H. et al. "Elongated Multiple Electronic Cascade and Cyclization Spacer Systems in Activatible Anticancer Prodrugs for Enhanced Drug Release" *J. Org. Chem.* (2001) 66:8815-8830.

Carl, P.L. et al. "A Novel Connector Linkage Application in Prodrug Design" *J. Med.Chem.* (May 1981) 24(5):479-480.

Toki, B.E. et al. "Protease-Mediated Fragmentation of ρ-Amidobenzyl Ethers: A New Strategy for the Activation of Anticancer Prodrugs" *J. Org. Chem.* (2002) 67:1866-1872.

Niculescu-Duvaz, D. et al. "Self-Immolative Nitrogen Mustard Prodrugs for Suicide Gene Therapy" *J. Med. Chem.* (1998) 41:5297-5309.

Boduszek, B. "Synthesis of Novel Phosphonopeptides Derived from Pyridylmethylphosphonate Diphenyl Esters" *Casreact.* (2001) 136:279691.

de Groot, F.M.H. et al. "Synthesis and Biological Evaluation of Novel Prodrugs of Anthracyclines for Selective Activation by the Tumor-Associated Protease Plasmin" *J. Med. Chem.* (1999) 42(25):5277-5283.

Liu, X.-J. et al. "Synthesis and Anticancer Activities of New 5-fluorouracil-1-yl Phosphonotripeptides" *Casreact.* (2002) 138:106974.

Meinnel, T. "Vers une conception rationnelle de nouveaux agents antibactériens" *Pathol. Biol.* (Oct. 1999) 47(8):780-783.

International Search Report dated Jan. 17, 2003 for PCT/US2002/014500.

Written Opinion dated Jun. 6, 2003 for PCT/US2002/014500.

International Preliminary Examination Report dated Oct. 31, 2003 for PCT/US2002/014500.

* cited by examiner

Figure 1

PEPTIDE DEFORMYLASE ACTIVATED PRODRUGS

CROSS-REFERENCE TO RELATED APPLICATIONS

This application claims the benefit under 35 U.S.C. §119 (e) to U.S. Provisional Application Ser. No. 60/290,099, filed May 9, 2001, the content of which is hereby incorporated by reference into the present disclosure.

TECHNICAL FIELD

The present invention relates to the field of Enzyme Catalyzed Therapeutic Activation (ECTA™) therapy and in particular, ECTA therapies specific for microorganisms that express Peptide Deformylase ("PDF").

BACKGROUND

Throughout this disclosure, various publications are referenced by first author and date, within parentheses, patent number or publication number. The complete bibliographic reference is given at the end of the application. The disclosures of these references are hereby incorporated by reference into this disclosure to more fully describe the state of the art to which this application pertains.

Enzyme Catalyzed Therapeutic Activation (ECTA™) therapy is a novel technology that provides unique prodrug substrates for target enzymes. Unlike conventional therapies, ECTA prodrugs neither inhibit nor irreversibly inactivate the target enzyme. U.S. Pat. Nos. 6,159,706; 6,245,750 and 6,339,151B1. See also PCT/US98/16607; PCT/US99/01332; and PCT/US00/20008.

Target enzymes convert the ECTA prodrug into a toxin preferentially within the target cell or in an environment wherein the target enzyme is expressed as compared to an environment where it is absent, as in an infected cell. Because the compounds do not require a targeting agent, they can be directly utilized, topically or systemically.

ECTA molecules do not, in most instances, yield cytotoxic products spontaneously (without target enzyme activation). They are not be appreciably activated by non-targeted enzymes, as this may result in toxicity to non-diseased or non-infected tissue. Table 1 summarizes the characteristics of ECTA molecules and enzyme activators.

TABLE 1

| Characteristics of ECTA Target Enzymes | Characteristics of ECTA Prodrugs |
| --- | --- |
| Infectious Disease: Must be present only in target cells (including diseased cells, bacteria, fungi, etc.). The enzyme should be necessary for continued viability or pathogenicity. | Must be able to get into cells (by itself or as prodrug). |
| Must process a molecule that resembles the natural substrate (an ECTA molecule) into cytotoxic species. The resemblance only has to be significant with respect to the specificity of the enzyme/substrate interaction and the ability of the enzyme to process the substrate intracellularly into toxic species. | At least one of the products formed from the enzymatic reaction must be cytotoxic. However, the ECTA remain in inactive form until activated by the target enzyme. The compound must have a high degree of specificity for the targeted enzyme, although conversion by a non-targeted enzyme is acceptable if the product(s) are not cytotoxic. |
| Must not be inactivated by the ECTA molecule, intermediate(s), or the product(s) of the reaction. | Must not inhibit or deactivate the targeted enzyme. |

In cases of bacterial, viral and fungal infections in plants, people or agriculturally important animals, metabolic pathways being present in the pathogenic organisms, but absent in the host are a source of potential ECTA target enzymes. For example, some pathways, as well as the enzymes involved, have only been found in bacteria, fungi and plants and not in mammalian cells. One example is the synthesis of "essential" amino acids—amino acids that animals cannot synthesize and must ingest with food. Nelson and Cox (1972).

Another example is Peptide Deformylase ("PDF", EC 3.5.1.31) which catalyses deformylation of N-terminal N-formyl methionine in a growing polypeptide chain. Meinnel (1999). The enzyme is present and active in bacteria (Meinnel et al, 1993), but has not been reported to be present in mammalian cells. Sequences homologous to bacterial PDF sequences have been recently found in mammals but their exact function is unknown. Giglione (2000a) and (2000b).

Because the enzyme is not active in humans it has been used as a target for antibacterial drugs, mostly PDF inhibitors. Dithiols can act as non-specific PDF inhibitors by coordination of sulfhydryl groups with the active site metal ion. Rajagopalan (1997). In case of 1,2- or 1,3-dithiols a slow extraction of the metal ion from the active site takes place. The formation of stable 5- or 6-membered rings, respectively, each containing two metal-sulfur bonds, accounts for this effect.

A rationally designed combinatorial library was used to select mechanism-based PDF inhibitors of the general structure HS—$CH_2$—$CH(R_a)$—CONH—$CH(R_b)$—CONH—$R_c$. Wei et al. (2000a). The optimal inhibitor selected from the library possesses an n-Bu group as an $R_a$, $R_b$=—$(CH_2)_3$—NH—C(=NH)—$NH_2$, and $R_c$ is 2-naphthalene. This compound acts as a competitive PDF inhibitor with a $K_i$ of 15 nM.

Jayasekera et al. (2000) describes a series of non-peptidic compounds structurally related to the known anticholesteremic thyropropic acid to inhibit *E. coli* PDF. Actinonin is reported to be a potent PDF inhibitor with activity in the subnanomolar $K_i$ range. Chen (2000).

Wei, et al. (2000a) describe that 5'-dipeptidyl derivatives of 5-fluorodeoxyuridine release a small molecule (5-fluorodeoxyuridine (5-F-dUrd)) upon PDF catalyzed deformylation. 5-F-dUrd formation was monitored in the reaction of the substrate catalyzed by purified PDF or *E. coli* crude lysates. The compound was marginally cytotoxic ($IC_{50}$>100 µM) when applied to *E. coli* bacteria. Potency was not increased by increased expression of PDF in bacteria (using a PDF-overexpressing strain). The compound was slightly more effective ($IC_{50}$=50 µM) against gram-positive microorgansims.

Additional inhibitors are described in Apfel et al. (2000), Apfel et al. (2001a), Apfel et al. (2001b), Clements et al. (2001), Durand et al. (1999), and Chen et al. (2000).

However, a compound or agent that is not an inhibitor but rather selectively and effectively activated by PDF to a toxin

DISCLOSURE OF THE INVENTION

This invention provides a prodrug compound having the structure:

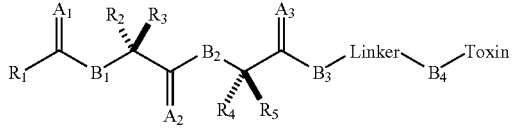

wherein $R_1$, $R_2$, $R_4$, and $R_5$ are independently the same or different and are selected from the group consisting of hydrogen, a substituted or unsubstituted $C_5$–$C_{14}$ aryl group and a substituted or unsubstituted, saturated or unsaturated $C_1$–$C_6$ alkyl group;

wherein $R_3$ is selected from the group consisting of a substituted or unsubstituted aryl group and a substituted or unsubstituted, saturated or unsaturated $C_1$–$C_6$ alkyl group and —$CH_2$—$CH_2$—X—$CH_3$, wherein X is selected from the group consisting of —O—, —S—, —NH—, —$NR_6$—, and —$CH_2$—; where $R_6$ is a lower alkyl;

wherein $A_1$ and $A_3$ are independently the same or different and are selected from the group consisting of =O, =S, =NH, =N—OH, or =N—$R_7$, where $R_7$ is hydrogen or a $C_1$–$C_6$ alkyl;

wherein $A_2$, is absent or selected from the group consisting of =O, =S; =NH, =N—OH, =N—$R_8$, or —$C(R_9)(R_{10})$—, wherein $R_8$, $R_9$, and $R_{10}$ are independently the same or different and are selected from the group consisting of hydrogen or a $C_1$–$C_6$ alkyl;

wherein $B_1$ is selected from the group consisting of —O—, —S—, —NH— or —$N(R_{11})$—, wherein $R_{11}$ is selected from the group consisting of hydrogen and a $C_1$–$C_6$ alkyl;

wherein $B_2$ is absent or is selected from the group consisting of —O—, —S—, —$N(R_{12})$—, or —$C(R_{13})(R_{14})$—, where $R_{12}$, $R_{13}$, and $R_{14}$ are independently the same or different and are selected from the group consisting of hydrogen or a substituted or unsubstituted, saturated or unsaturated alkyl;

wherein the fragment —$B_2$—$C(R_4)(R_5)$—$C(=A_3)$— in its entirety is a naturally occurring amino acid such as proline, a derivative or analog thereof, or a peptidomimetic thereof;

wherein the fragment —$B_2$—$C(R_4)(R_5)$—$C(=A_3)$— in its entirety is proline, a derivative or analog thereof, or a peptidomimetic thereof;

wherein $B_3$ is absent or is selected from the group consisting of —O—, —S—, or —NH—, or —$N(R_{15})$—, wherein $R_{15}$ is selected from the group consisting of hydrogen and a $C_1$–$C_6$ alkyl;

wherein $B_4$ is absent or is selected from the group consisting of —O—, —S—, —$N(R_6)$—, and —$C(R_{16})(R_{17})$— and wherein $R_{16}$ and $R_{17}$ are independently the same or different and are selected from the group consisting of hydrogen or a substituted or unsubstituted, saturated or unsaturated alkyl;

wherein a linker is absent or is a traceless linker is selected from the group consisting of, but not limited to, —$C_6H_4$—$CH_2$— and —$C_6H_4$—$CH_2$—$X_1$—$C(=X_2)$— wherein $X_1$ and $X_2$ are independently the same or different are selected from the group consisting of —O—, —S— and —N(Ra) where $R_a$ is -hydrogen or a lower alkyl, and —$(CH_2)_n$—$NR_b$—(C=O)— which has the structure:

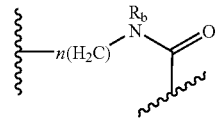

wherein n=2 or 3 and $R_b$ is hydrogen or a lower alkyl;

and wherein a toxin is intended to include any agent that is toxic to a cell upon release by an "activating" enzyme, with the proviso that the toxin is not 5-fluorodeoxyuridine (5-F-dUrd).

In one aspect, the compound is as noted above but that $R_1$ and $R_2$ are both hydrogen.

In a further aspect, the compound is as noted above but that $R_3$ is —$CH_2$—$CH_2$—X—$CH_3$, wherein X is selected from the group consisting of oxygen, sulfur or methylene. In a yet further aspect, the compound is as noted above but that X is sulfur.

In one aspect, the compound is as noted above but that $A_1$ and $A_2$ are both oxygen.

In a further aspect, the compound is as noted above but that $B_1$ is —NH—.

In a further aspect, the compound is as noted above but that $B_4$ is absent.

In a further aspect, the toxin is selected from the group consisting of 2-mercaptopyridine-N-oxide, ciprofloxacin, norfloxacin, and nitrogen mustard, and the derivatives and analogues thereof.

In one aspect, the compound is as noted above but that $B_2$ is —NH, $B_3$ is —O—, $R_4$ is 2-methyl-propyl and $R_5$ is hydrogen.

In one aspect, the compound is as noted above but that $R_4$ is 2-methyl-propyl and $R_5$ is hydrogen.

Also provided by this invention is a method for inhibiting the growth of a microorganism that expresses PDF by contacting the microorganism with an effective amount of the compound as describe above. This method inhibits the growth of gram-positive and gram-negative microorganism, e.g., of *S. aureus, S. epidermidis, K. pneumoniae, E. aerogenes, E. cloacae, M. catarrhalis, E. coli, E. faecalis, H. influenzae* and *P. aeruginosa*. This method can be practiced in vitro, ex vivo and in vivo. Further provided is a method for alleviating the symptoms of an infection by a PDF expressing microorganism in a subject by administering or delivering to the subject an effective amount of the compound described above. A "subject" is defined herein and includes mammals such as human patients.

This invention also provides a composition comprising the prodrug compounds as described above, alone or in combination with other compounds or other agents, known or yet to be discovered, and a carrier. In one aspect, the carrier is another molecule or an inert substance such as a plate or column. In an alternative embodiment, the carrier is a pharmaceutically acceptable carrier. Pharmaceutically acceptable carriers are known in the art and described briefly above.

BRIEF DESCRIPTION OF THE FIGURES

FIG. 1 is a proposed reaction scheme for PDF activation of the compounds of this invention.

MODES FOR CARRYING OUT THE INVENTION

Figure 2:
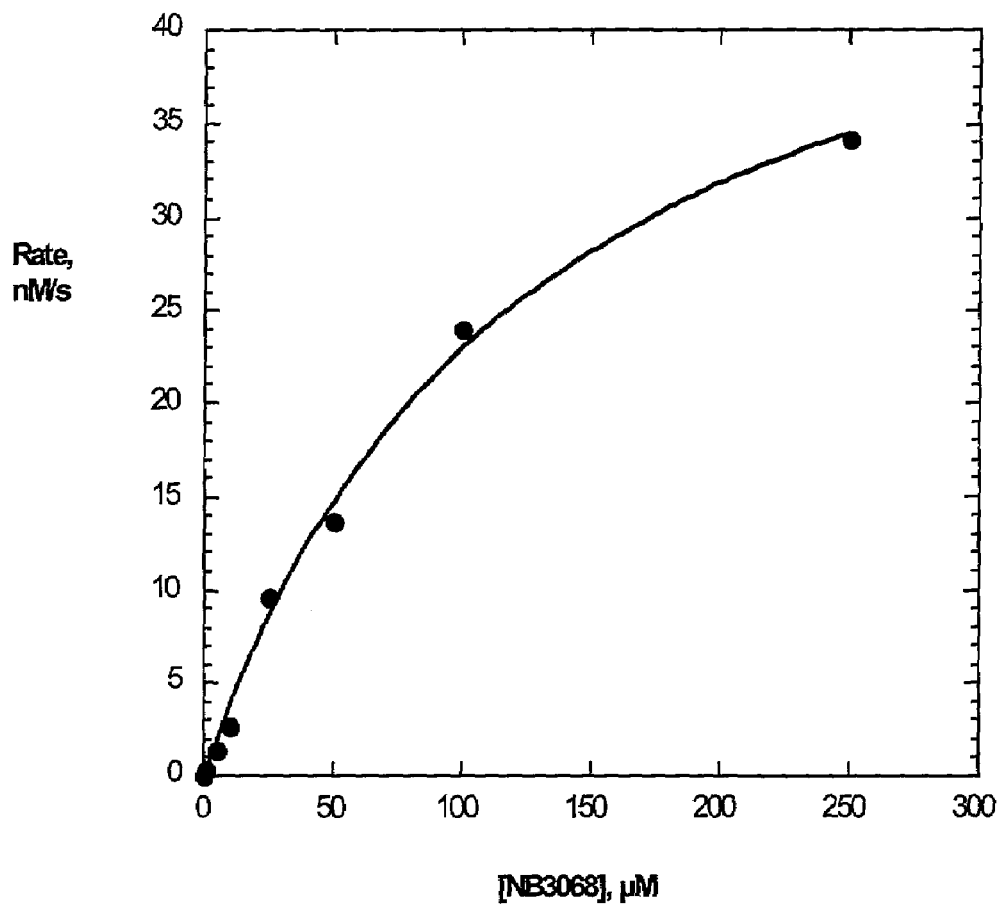
FIG. 2 showns dependence of the rate of NB3068 reaction catalyzed by purified PDF on NB3068 concentration.

The practice of the present invention will employ, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "MOLECULAR CLONING: A LABORATORY MANUAL" Second Edition (Sambrook et al., 1989); "OLIGONUCLEOTIDE SYNTHESIS" (M. J. Gait, ed., 1984); "ANIMAL CELL CULTURE" (R. I. Freshney, ed., 1987); the series "METHODS IN ENZYMOLOGY" (Academic Press, Inc.); "HANDBOOK OF EXPERIMENTAL IMMUNOLOGY" (D. M. Weir & C. C. Blackwell, eds.); "GENE TRANSFER VECTORS FOR MAMMALIAN CELLS" (J. M. Miller & M. P. Calos, eds., 1987); "CURRENT PROTOCOLS IN MOLECULAR BIOLOGY" (F. M. Ausubel et al., eds., 1987, and periodic updates); "PCR: THE POLYMERASE CHAIN REACTION" (Mullis et al., eds., 1994); "CURRENT PROTOCOLS IN IMMUNOLOGY" (J. E. Coligan et al., eds., 1991); J. March, ADVANCED ORGANIC CHEMISTRY: REACTIONS, MECHANISMS AND STRUCTURE, $4^{th}$ edition (John Wiley & Sons, NY (1992)).

As used herein, certain terms may have the following defined meanings.

The singular form "a," "an" and "the" include plural references unless the context clearly dictates otherwise. For example, the term "a cell" includes a plurality of cells, including mixtures thereof.

The term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used herein, the term "peptidomimetic" refers to a compound containing non-peptidic structural elements that is capable of mimicking or antagonizing the biological action(s) of a natural parent peptide.

As used herein, the term "substituents" includes, but is not limited to halogen atoms and halomethyl groups such as $CF_3$ and $CCl_3$; oxygen containing groups such as oxo, hydroxy, carboxy, carboxyalkyl, alkoxy, alkoyl, alkoyloxy, aryloxy, aryloyl, and aryloyloxy; nitrogen containing groups such as amino, alkylamino, dialkylamino, cyano, azide and nitro; sulfur containing groups such as thiol, alkylthiol, sulfonyl and sulfoxide; heterocyclic groups which may themselves be substituted; alkyl groups which may themselves be substituted; and aryl groups which may themselves be substituted.

The term "alkyl" refers to any branched or unbranched, cyclic or acyclic, saturated (alkyl) or unsaturated (alkayl, alkenyl or alkynyl) hydrocarbyl radical. This term is not limited to a monovalent radical. Where cyclic, the alkyl group is $C_3$ to $C_{12}$. Where acyclic, the alkyl group is $C_1$ to $C_{16}$. The term "alkoxy" and "aryloxy" means alkyl-O and aryl-O groups, respectively. Reference to "alkoyl" and "aryloyl" groups means alkyl-CO and aryl-CO, respectively.

The term "aryl" refers to an aromatic group, such as phenyl or napthyl, or a heteroatomic group containing one or more heteroatom, such as pyridyl, pyrrolyl, furanyl and thiophenyl. This term is not limited to a monovalent radical. The term "aromatic" refers to any compound characterized by the presence of at least one benzene ring. Examples of aromatic groups include, but are not limited to, benzene and naphthalene.

The alkyl and aryl groups may be substituted or unsubstituted. The term "aliphatic" refers to any and all organic compounds of hydrogen and carbon characterized by a straight chain of the carbon atoms. The subgroups of "aliphatic" compounds includes alkanes, alkenes, and alkynes. The aliphatic groups may be unsubstituted or substituted. See above for examples of substituents.

The term "alicyclic" refers to and covers any and all organic compounds of hydrogen and carbon atoms joined to form one or more rings. The alicyclic groups may be unsubstituted or substituted. See above for examples of substituents.

"Cycloalkyl" is intended to include saturated ring groups, such as cyclopropyl, cyclobutyl, or cyclopentyl. This term is not limited to a monovalent radical. The cycloalkyl groups may be unsubstituted or substituted. See above for examples of substituents.

The term "alkenyl" refers to normal alkenyl, branch chain alkenyl and cycloalkenyl groups having one or more sites of unsaturation. "Alkynyl" is intended to include hydrocarbon chains of either a straight or branched configuration and one or more triple carbon-carbon bonds which may occur in any stable point along the chain, such as ethynyl and propynyl. These terms are not limited to monovalent radicals. The alkenyl or alkynyl groups may be unsubstituted or substituted. See above for examples of substituents.

"Lower alkyl" means the above-defined broad definition of alkyl groups having 1 to 6 carbons in case of normal lower alkyl, and as applicable 3 to 6 carbons for lower branch chained (e.g., 2-methyl-propane) and cycloalkyl groups. "Lower alkenyl" is defined similarly having 2 to 6 carbons for normal lower alkenyl groups, and 3 to 6 carbons for branch chained and cyclo-lower alkenyl groups. "Lower alkynyl" is also defined similarly, having 2 to 6 carbons for normal lower alkenyl groups, and 4 to 6 carbons for branch chained lower alkynyl groups. The lower alkyl, alkenyl and alkynyl groups may be unsubstituted or substituted. See above for examples of substituents.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2V+1)). The term haloalkyl is not limited to a monovalent radical. "Halogen" includes fluorine, chlorine, bromine, iodine and astatine. Examples of haloalkyl include, but are not limited to, trifluoromethyl, trichloromethyl, pentafluoroethyl, and pentachloroethyl.

The term "heterocyclic" refers to any compound in which the ring structure is a combination of more than one kind of atom. Examples of heterocyclic compounds include, but are not limited to, pyridine, furan and pyrrole. This term is not limited to a monovalent radical. The heterocyclic groups may be unsubstituted or substituted. See above for definition of substituents.

As used herein the term "prodrug" means a precursor or derivative form of a pharmaceutically active agent or substance that is less cytotoxic to a target cell as compared to the drug metabolite and is capable of being enzymatically activated or converted into the more active form.

A "composition" is intended to mean a combination of active agent and another compound or composition, inert (for example, a surface, a paint, a detectable agent or label or a pharmaceutically acceptable carrier) or active, such as an adjuvant or disinfectant.

A "pharmaceutical composition" is intended to include the combination of an active agent with a carrier, inert or active, making the composition suitable for diagnostic or therapeutic use in vitro, in vivo or ex vivo.

The term "prophylactically effective amount" refers to an amount effective in preventing infection in a subject or plant infestation.

The term "pharmaceutically acceptable carrier" and "biologically acceptable carrier" refer to a carrier or adjuvant that is administered to a host or patient, together with a compound of this invention, and which does not destroy the pharmacological activity thereof and is non-toxic, when administered in doses sufficient to deliver an effective amount of the compound. Examples of suitable carriers include liquid phase carriers, such as sterile or aqueous solutions, as well as those described below. Examples of pharmaceutically acceptable carrier include any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARM. SCI., 15th Ed. (Mack Publ. Co., Easton (1975)).

The term "treating" refers to any of the following: the alleviation of symptoms of a particular disorder in a patient; the improvement of an ascertainable measurement associated with a particular disorder; or a reduction in microbial number. One of skill in the art can determine when a host has been "treated" by noting a reduction in microbial load or an alleviation in symptoms associated with infection.

The term "pharmaceutically acceptable salt, prodrug or derivative" relates to any pharmaceutically acceptable salt, ester, ether, salt of an ester, solvate, such as ethanolate, or other derivative of a compound of the present invention which, upon administration to a recipient, is capable of providing (directly or indirectly) a compound of this invention or an active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system).

Salts of the compounds of the present invention may be derived from inorganic or organic acids and bases. Examples of acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts. Examples of bases include alkali metal (e.g., sodium) hydroxides, alkaline earth metal (e.g., magnesium) hydroxides, ammonia, compounds of formula $NW_4^+$, wherein W is $C_{1-4}$ alkyl and THAM (2-amino-2-hydroxymethyl-1,3-propanediol).

Examples of salts include: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylproprionate, picrate, pivalate, propionate, succinate, tartrate, thiocyanate, tosylate and undecanoate. Other examples of salts include anions of the compounds of the present invention compounded with a suitable cation such as $Na^+$, $Li^+$, $NH_4^+$, and $NW_4^+$ (wherein W is a $C_{1-4}$ alkyl group).

For therapeutic use, salts of the compounds of the present invention will be pharmaceutically acceptable. However, salts of acids and bases which are non-pharmaceutically acceptable may also find use, for example, in the preparation or purification of a pharmaceutically acceptable compound or for use to reduce microbial infestation in plants.

The term "traceless Linker" indicates a spacer or connector between two parts of a single molecule such that when a particular bond is severed between the two parts of the molecule, the connector which is still attached to the second part of the molecule, eliminates leaving no trace of itself. See, for example, de Groot et al. (2000).

The term "effective amount" is to include therapeutically or prophylactically effective amounts. The term refers to an amount effective in treating or preventing an infection in a patient or an infestation in a plant either as monotherapy or in combination with other agents.

"Inhibiting the growth" of a microorganism means reducing by contact with an agent, the rate of proliferation of such a microorganism, in comparison with a control microorganism of the same species not contacted with this agent.

A "subject" is any living being that is or can be a direct or indirect host to a PDF expressing microorganism, including plants and animals such as a fish, an avian or a mammal, and preferably a human. Fish include, but are not limited to pets and aquaculture. Avians include, but are not limited to pets, sport animals and farm animals. Mammals include, but are not limited to, murines, simians, humans, farm animals, sport animals, and pets.

Examples include, but are not limited to non-vertebrates, vertebrates, e.g., avians or mammals, such as human patients. Mammals include, but are not limited to, murines, simians, humans, farm animals, sport animals, and pets.

PDF is a well-studied enzyme. The crystallographic structure of it is known. Chan et al. (1997). The enzyme has been expressed in *E. coli* BL21(DE3) cells Rajagopalan et al. (1997). The authors of the paper isolated the *E. coli* def gene by PCR using the primers designed based on the literature data on the sequence of the gene. The purified enzyme is unstable due to fast oxidation the catalytic site $Fe^{2+}$ by the atmospheric oxygen. Rajagopalan et al. (1998). The conditions for proper handling the enzyme to avoid inactivation have been reported. Rajagopalan et al. (1997). Importantly, $Zn^{2+}$ and $Ni^{2+}$ containing PDF's are stable allowing for the in vitro evaluation of the enzyme catalytic properties. There exists a simple continuous colorimetric assay for PDF. Wei et al. (1997). It utilizes N-formylmethionylleucine p-nitroanilide as a substrate. A coupled aminopeptidase reaction that follows the PDF reaction releases p-nitroaniline that can be monitored spectrophotometrically at 405 nm.

Figure 1:
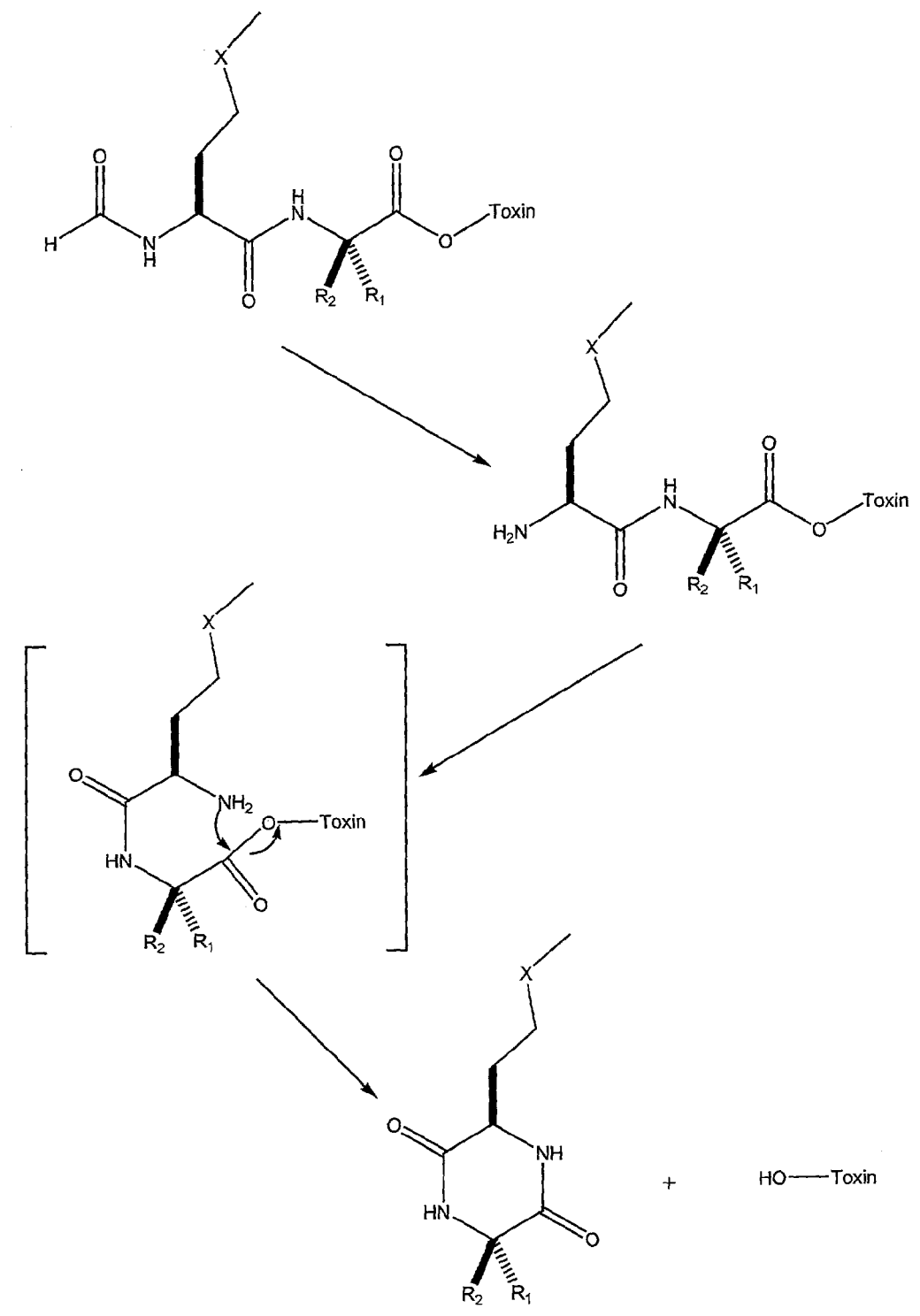

PDF is a perfect ECTA target enzyme. It is active in bacteria and inactive in human hosts. It has broad substrate specificity. Deformylation liberates a free amino group of methionine (or another amino acid or an amino acid analog tolerated as an $R_3$ of the substrate, such as norleucine) which can perform a subsequent nucleophilic attack. With a rationally designed dipeptide or an equivalent peptidomimetic fragment of the substrate the free amino group can attack an optimally positioned carbonyl group of the substrate thus forming a cyclic molecule (e.g. diketopiperazine, DKP) and releasing a toxin. The substrate can be optimized to enhance cyclization. The scheme of the proposed reaction exemplifying a dipeptide-based substrate is given in FIG. 1. Here X can be, for example, sulfur (methionine) or —$CH_2$— (norleucine). $R_1$ and $R_2$ are aliphatic radicals that can be selected based on the published SAR data for PDF. Hu et al. (1998).

Thus, in one aspect, the invention provides a prodrug compound having the structure:

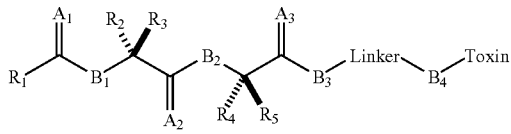

wherein $R_1$, $R_2$, $R_4$, and $R_5$ are independently the same or different and are selected from the group consisting of hydrogen, a substituted or unsubstituted $C_5$–$C_{14}$ aryl group, a heteroaryl (for example, phenylmethylene, 4-hydroxypropyl, 3-aminopropyl, N-methyl-3-aminoethyl, 2-methoxymethyl, etc.), and a substituted or unsubstituted, saturated or unsaturated $C_1$–$C_6$ alkyl group (for example, methyl, ethyl, 3-hydroxypropyl, 3-aminopropyl, N-methyl-3-aminoethyl, 2-methoxymethyl, etc.);

wherein $R_3$ is selected from the group consisting of a substituted or unsubstituted aryl group (for example, phenylmethyl, triazolemethylene, thiophenemethylene, etc.), and a substituted or unsubstituted, saturated or unsaturated $C_1$–$C_6$ alkyl group (for example ethyl, propyl, 2-hydroxyethyl, etc.) and —$CH_2$—$CH_2$—X—$CH_3$, wherein X is selected from the group consisting of —O—, —S—, —NH—, —$NR_6$—, and —$CH_2$—; where $R_6$ is a lower alkyl such as methyl or ethyl for example;

wherein $A_1$ and $A_3$ are independently the same or different and are selected from the group consisting of =O, =S, =NH, =N—OH, or =N—$R_7$, where $R_7$ is hydrogen or a $C_1$–$C_6$ alkyl, for example, methyl, ethyl or methoxymethyl;

wherein $A_2$, is absent or selected from the group consisting of =O, =S; =NH, =N—OH, =N—$R_8$, or —$C(R_9)$($R_{10}$)—, wherein $R_8$, $R_9$, and $R_{10}$ are independently the same or different and are selected from the group consisting of hydrogen or a $C_1$–$C_6$ alkyl for example methyl, ethyl or methoxymethyl;

wherein $B_1$ is selected from the group consisting of —O—, —S—, —NH— or —N($R_{11}$)—, wherein $R_{11}$ is selected from the group consisting of hydrogen and a $C_1$–$C_6$ alkyl for example methyl, ethyl or methoxymethyl;

wherein $B_2$ is absent or is selected from the group consisting of —O—, —S—, —N($R_{12}$)—, or —C($R_{13}$)($R_{14}$)—, where $R_{12}$, $R_{13}$, and $R_{14}$ are independently the same or different and are selected from the group consisting of hydrogen or a substituted or unsubstituted, saturated or unsaturated alkyl for example methyl, ethyl or methoxymethyl;

wherein the fragment —$B_2$—C($R_4$)($R_5$)—C(=$A_3$)— in its entirety is one of the twenty naturally occurring amino acids, e.g., proline, an analog, derivative or peptidomimetic thereof;

wherein the fragment —$B_2$—C($R_4$)($R_5$)—C(=$A_3$)— in its entirety is proline, an analog, derivative or peptidomimetic thereof;

wherein $B_3$ is absent or is selected from the group consisting of —O—, —S—, or —NH—, or —N($R_{15}$)—, wherein $R_{15}$ is selected from the group consisting of hydrogen and a $C_1$–$C_6$ alkyl for example methyl, ethyl or methoxymethyl;

wherein $B_4$ is absent or is selected from the group consisting of —O—, —S—, —N($R_6$)—, and —C($R_{16}$)($R_{17}$)— wherein $R_{16}$ and $R_{17}$ are independently the same or different and are selected from the group consisting of hydrogen or a substituted or unsubstituted, saturated or unsaturated alkyl, for example methyl, ethyl or methoxymethyl;

wherein a linker is absent or is a traceless linker is selected from the group consisting of, but not limited to, —$C_6H_4$—$CH_2$— and —$C_6H_4$—$CH_2$—$X_1$—C(=$X_2$)— wherein $X_1$ and $X_2$ are independently the same or different are selected from the group consisting of —O—, —S— and —N($R_a$) where $R_a$ is -hydrogen or a lower alkyl; and —$(CH_2)_n$—$NR_b$—(C=O)— which has the structure:

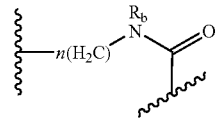

wherein n=2 or 3 and $R_b$ is hydrogen or a lower alkyl;

and wherein a toxin is a cytotoxic or antibiotic molecule that is released upon activation by an enzyme, with the proviso that the toxin is not 5-F-dUrd.

Examples of toxins include, but are not limited to a group consisting of fluorquinolones, aminogylcosides, mitomycin, CC-1065, ducarmycin, CBI analogs, anthracyclins, vinca alkaloids, mitomycins, bleomycins, penicillins, cephalosporins, oxacillins, carbopenems, tetracyclins, chloramphenicols, macrolides, cycloserines, fluoroquinolones (including, but not limited to, ciprofloxacin and norfloxacin), glycopeptides, aminoglycosides, peptide antibiotics, oxazolidinones, quinolones, sulfonamides, cytotoxic nucleosides, pteridine family, nitrogen mustards, polyhalogenated biaryl ethers, diynenes, podophillotoxins, taxoids, doxorubicin, carminomycin, daunorubicin, aminopterin, methotrexate, methopterin, dichloromethotrexate, mitomycin C, porfiromycin, 6-mercaptopurine, cytosine arabinoside, podophillotoxin, etoposide, etoposide phosphate, melphalan, vindesine, vinblastine, vincristine, leurosidine, leurosine, bis-(2-chloroethyl)amine, trichlorcarban, trichlorocarbanilide, tribromosalicylanilide, sulphamethoxazole, chloramphenicol, cycloserine, trimethoprim, chlorhexidine, hexachlorophene, fentichlor, 5-chloro-2-(2,4-dichlorophenoxy)phenol, 4-chloro-2-(2,4-dichlorophenoxy)phenol, 3-chloro-2-(2,4-dichlorophenoxy)phenol, 6-chloro-2-(2,4-dichlorophenoxy)phenol, 5-chloro-2-(3,4-dichlorophenoxy) phenol, 5-chloro-2-(2,5-dichlorophenoxy)phenol, 5-chloro-2-(3,5-dichlorophenoxy)phenol, 2,2'-dihydroxy biphenyl ether, halogeneted 2-hydroxybenzophenones, 2-mercaptopyridine-N-oxide, combretastatin, camptothesin, apoptolidene, cisplatin, epothilone, halichondrin, hemiasterlin, methioprim, thapsigargin, chloroquine, 4-hydroxycyclo-phosphamide, etoposide, colchicine, melphalan, quercetin, genistein, erbstatin, N-(4-aminobutyl)-5-chloro-2-naph-talen-sulfonamide, pyridinyloxazol-2-one, isoquinolylox-azolone-2-one, verapamil, quinine, quinidine, and chloro-quine.

In a further aspect, the compound is as noted above but the toxin is selected from the group consisting of 2-mercapto-pyridine-N-oxide, ciprofloxacin, norfloxacin, and nitrogen mustard, and the derivatives and analogs thereof.

In one aspect, the compound is as noted above but $B_2$ is —NH, $B_3$ is —O—, $R_4$ is 2-methyl-propyl and $R_5$ is hydrogen.

In one aspect, the fragment —$B_2$—$C(R_4)(R_5)$—C(=$A_3$)— in its entirety is a naturally occurring amino acid such as proline, a derivative or analog thereof, or a pepti-domimetic thereof In one aspect, wherein the fragment —$B_2$—$C(R_4)(R_5)$—C(=$A_3$)— in its entirety is proline, a derivative or analog thereof, or a peptidomimetic thereof;

In one aspect, the compound has the structure as set forth above, with the proviso that the toxin is selected from the group of structures consisting of:

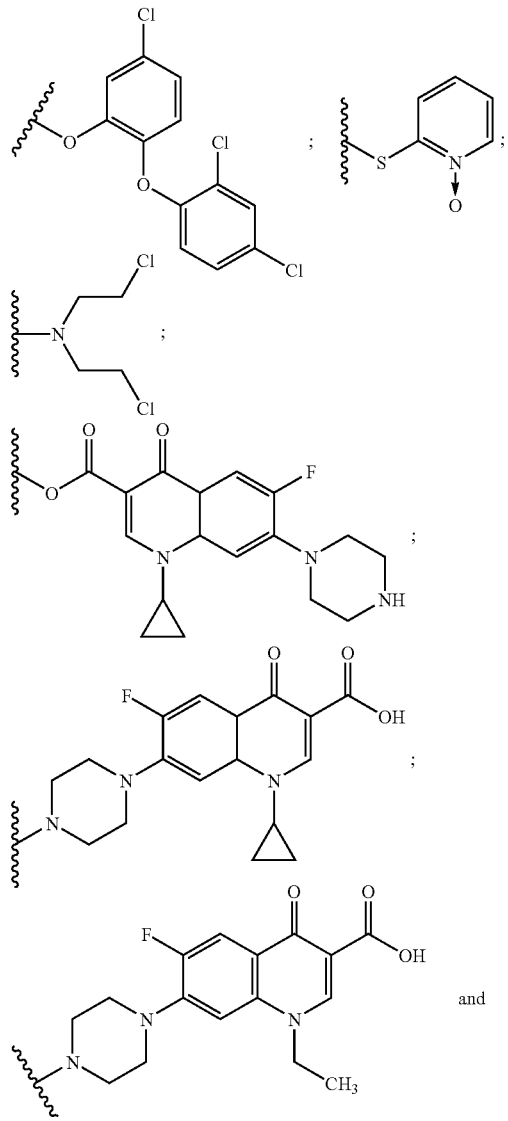

-continued

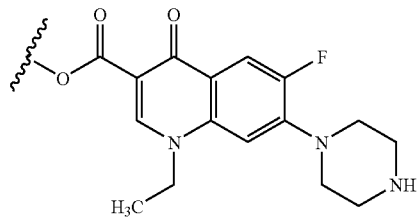

and derivatives, analogs and salts thereof. It will be appreciated that various modifications to the above toxins can be made without an appreciable loss of activity.

In one aspect, the compound is as noted above but $R_1$ and $R_2$ are both hydrogen.

In a further aspect, the compound is as noted above but $R_3$ is —$CH_2$—$CH_2$—X—$CH_3$, wherein X is selected from the group consisting of oxygen, sulfur or methyl. In a further aspect, X is sulfur.

In a further aspect, the compound is as noted above but $A_1$ and $A_2$ are both oxygen.

In a further aspect, the compound is as noted above but $B_1$ is —NH—.

In a further aspect, the compound is as noted above but the linker has the following structure:

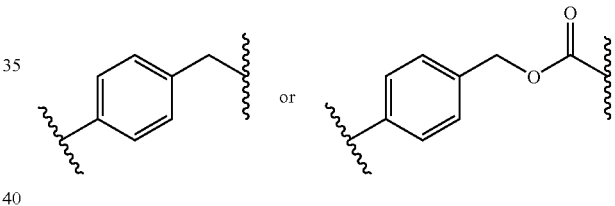

In a further aspect, the compound is as noted above but $B_4$ is absent.

In one aspect, the compound is 2-(2-formylamino-4-methylsulfanyl-butyrylamino)-4-methyl-pentanoic acid 4-(N-oxide-pyridin-2-ylsulfanylmethyl)-phenyl ester compound and has the structure:

NB3024

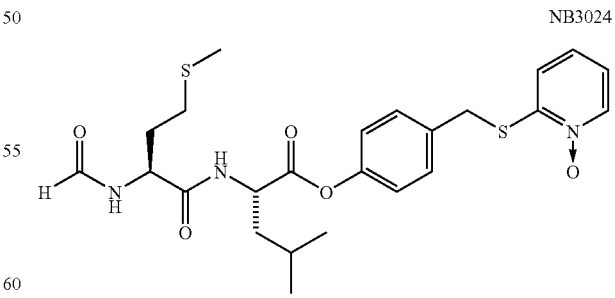

In another aspect, the compound is 1-cyclopropyl-6-fluoro-4-oxo-7-piperazin-1-yl-1,4,4a,8a-tetrahydro-quino-line-3-carboxylic acid 4-[2-(2-formylamino-4-methylsulfa-nyl-butyrylamino)-4-methyl-pentanoyloxy]-benzyl ester that has the structure:

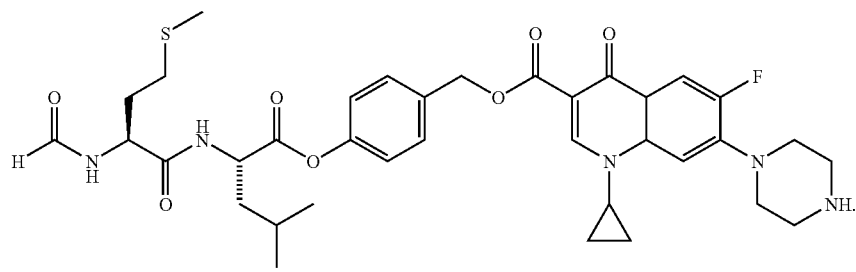

In one aspect, the compound is 1-ethyl-6-fluoro-7-(4-{4-[2-(2-formylamino-4-methylsulfanyl-butyrylamino)-4-methyl-pentanoyloxy]-benzyloxycarbonyl}-piperazin-1-yl)-4-oxo-1,4-dihydro-quinoline-3-carboxylic acid that has the structure:

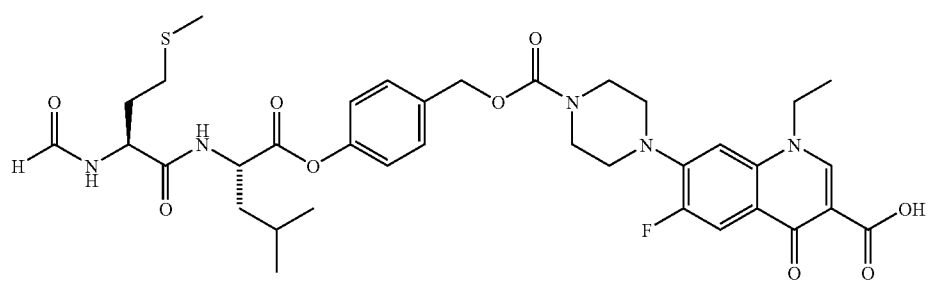

In a further aspect, the compound is tert-butoxycarbonylamino-4-methyl-pentanoic acid-5-chloro-2-(2,4-dichloro-phenoxy)-phenyl ester and has the structure:

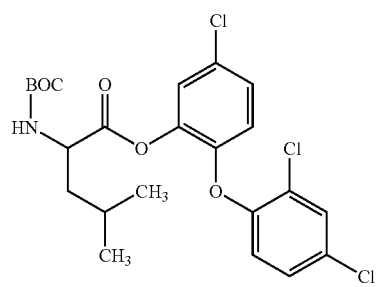

In another aspect, the compound is 2-(2-formylamino-4-methylsulfanyl-butyrylamino)-4-methyl-pentanoic acid 5-chloro-2-(2,4-dichloro-phenoxy)-phenyl ester and has the structure:

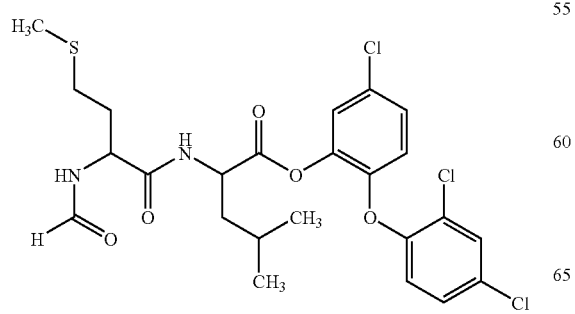

In one aspect, the compound is 2-(2-formylamino-4-methylsulfanyl-butyrylamino)-4-methyl-pentanoic acid 4-{[bis-(2-chloro-ethyl)-carbamoyloxy]-methyl}-phenyl ester and has the structure:

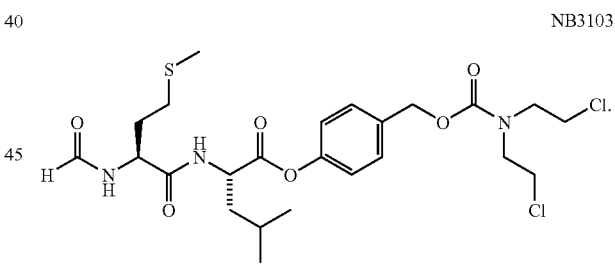

In a further aspect, the compound is -tert-Butoxycarbonylamino-4-methyl-pentanoic acid 4-formyl-phenyl ester and has the structure:

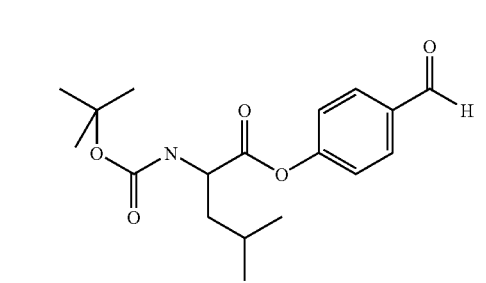

In a further aspect, the compound is 2-(2-formylamino-4-methylsulfanyl-butyrylamino)-4-methyl-pentanoic acid 4-hydroxymethyl-phenyl ester which has the structure:

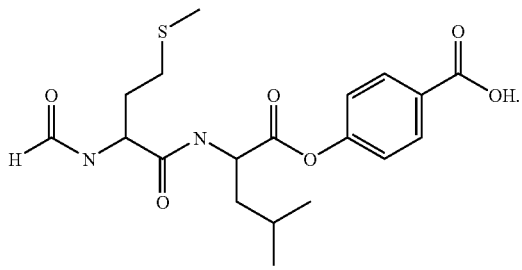

In a further aspect, the compound is 2-(2-Formylamino-4-methylsulfanyl-butyrylamino)-4-methyl-pentanoic acid 4-chloromethyl-phenyl ester and has the structure:

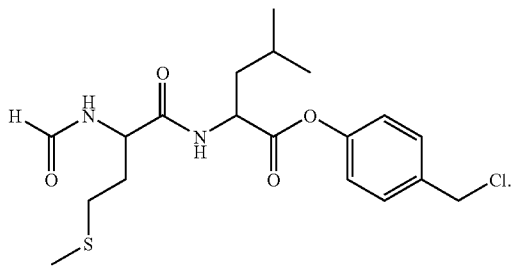

Any of the above noted compounds can be combined with a carrier, such as a pharmaceutically acceptable carrier or an additional effective agent such as an antibiotic. These compounds and compositions are also useful to be used in combination with known or yet to be discovered therapeutics and therapeutic methods to enhance the therapy or efficacy of the drug.

Also provided by this invention is a method for inhibiting the growth of a PDF expressing microorganism by contacting the microorganism with an effective amount of the compound as describe above. Methods to detect PDF expression are known in the art. See, for example, Wei, et al. (1997). This method is particularly useful in inhibiting the growth of gram-positive and gram-negative microorganisms, e.g., of *S. aureus, S. epidermidis, K. pneumoniae, E. aerogenes, E. cloacae, M. catarrhalis, E. coli, E. faecalis, H. influenzae* and *P. aeruginosa*. and those identified in Table 2, below. Further provided is a method for alleviating the symptoms of an infection in a subject, wherein the infection is caused by a PDF expressing microorganism, by administering or delivering to the subject an effective amount of the compound described above. Also provided by this invention is a method for treating an infection caused by a PDF expressing microorganism by administering or delivering to the subject an effective amount of the compound described above. A "subject" is defined above and includes mammals such as human patients. Examples of PDF expressing microorganims and the corresponding diseases and symptoms caused by infection by these microorganisms, are provided in Table 2, below.

TABLE 2

| PDF Expressing Microorganism | Disease or Symptom Caused by Infection |
|---|---|
| Gram-Positive | |
| *Staphylococcus aureus* | major human pathogen, bacteremia, pneumonia |
| *Staphylococcus epidermidis* and other coagulase-negative _i staphylococci | urinary tract infections, osteomyelitis, bacteremia |
| *Streptococcus pyogenes* | bacteremia, lymphagitis, pneumonia |
| *Streptococcus pneumoniae* | pneumonia, otitis media, sinusitis |
| *Streptococcus agalactiae* | primary bacteremia, pneumonia, endocarditis, osteomyelitis |
| *Enterococcus* species | urinary tract infections, bacteremia, endocarditis, intra-abdominal and pelvic infections, neonatal sepsis |
| Gram-Negative | |
| *Neisseria gonorrhoeae* | genital infection, perihepatitis |
| *Moraxella catarrhalis* | otitis media, lower respiratory tract infections, pneumonia, bacteremia |
| *Campylobacter jejuni* | acute enteritis, acute colitis, bacteremia |
| *Enterobacteriaceae* (including *Escherichia, Salmonella, Klebsiella, Enterobacter*) | enteric infections, urinary tract infections, respiratory infections, bacteremia |
| *Pseudomonas aeruginosa* | endocarditis, respiratory infections, bacteremia, central nervous system infections |
| *Acinetobacter* species | respiratory tract infections, bacteremia, genitourinary |
| *Haemophilus influenzae* | meningitis, epiglottitis, pneumonia, bacteremia |

This invention also provides a composition comprising the prodrug compounds as described above, alone or in combination with other compounds or other agents, known or yet to be discovered, and a carrier. In one embodiment, the carrier is a pharmaceutically acceptable carrier.

In the clinical use of the prodrug, antibiotics will likely follow well established guidelines. Dosage will likely be similar to those already employed for most other antibiotics. It is estimated that a dose of prodrug will be in the range of 100 µg to 100 mg to 1 gm, or given once every eight hours, or once a day, for one or two weeks, or until the patient tests negative for infectious organisms.

In one aspect, the invention encompasses a method of treating or protecting plants from infections caused by PDF expressing microorgansims by applying an effective amount of the substrate prodrug.

In order to achieve good dispersion and adhesion of the compounds as used to treat plants, it may be advantageous to formulate the compounds with components that aid dispersion and adhesion. Suitable formulations will be known to those skilled in the art.

This invention also provides a method for treating or protecting plants from infection by microorganisms expressing PDF by applying an effective amount of the prodrug compound to the foliage, roots or the soil surrounding the plants or roots. These isolated compounds can be combined with known pesticides or insecticides.

Compounds within the present invention when used to treat or protect plants from infections caused by PDF expressing microorganisms can be formulated as wettable powders, granules and the like, or can be microencapsulated in a suitable medium and the like. Examples of other formulations include, but are not limited to soluble powders, wettable granules, dry flowables, aqueous flowables, wettable dispersible granules, emulsifiable concentrates and aqueous suspensions. Other suitable formulations will be known to those skilled in the art.

This invention further provides a method for administering the prodrug compound to fish in an amount effective to either prevent or treat an infection caused by PDF expressing microorganisms. The compound may be administered by incorporating the compound into the food supply for the fish. Alternatively, the compound may be added to the water in which fish live, or are contained within. Finally, the compound may be administered to the fish as a suitable pharmaceutical preparation. Other suitable formulations will be known to those skilled in the art.

Further provided is a process for producing the prodrugs of this invention. In general the process requires the following steps:

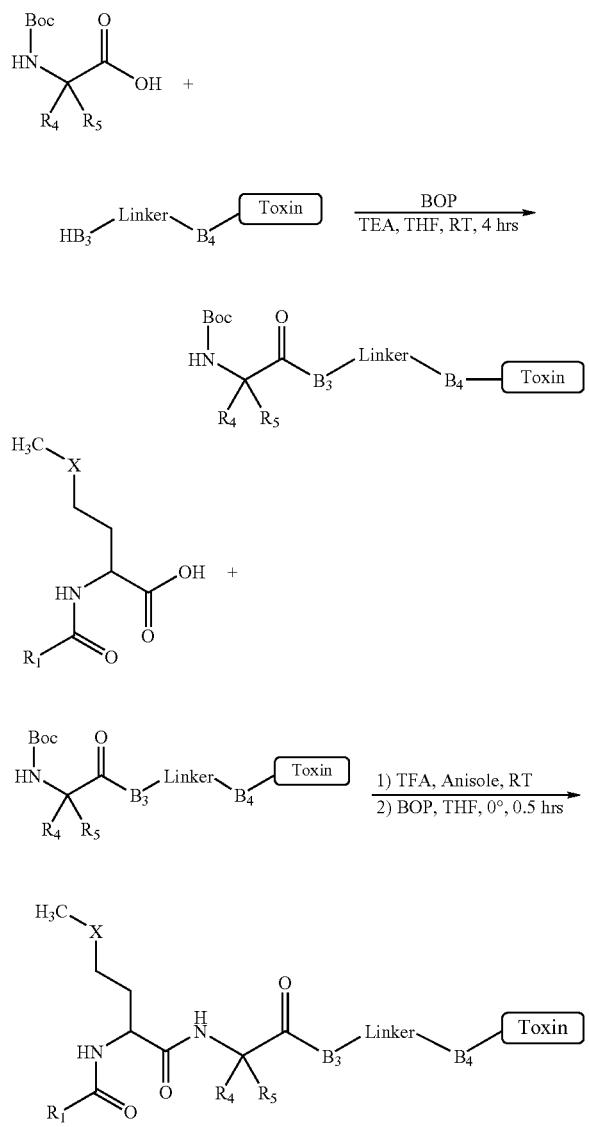

With respect to the above diagram, X can be sulfur (methionine) or —CH$_2$— (norleucine). R$_1$ through R$_5$ and B$_1$ through B$_3$ are as defined above. Reaction conditions and full names for the abbreviations can be found in the experimental examples infra.

This invention provides a method for identifying potential therapeutic agents that inhibit the growth of an organism expressing PDF by contacting a sample containing the PDF expressing microorganism with an effective amount of a candidate prodrug compound. In a separate sample, the same microorganism is contacted with an effective amount of a prodrug of this invention. If the agent has comparable anti-proliferative ability as compared to a prodrug as described herein, the candidate is useful to useful to inhibit the growth or kill a PDF-expressing microorganism.

The prodrug is contacted with the sample under conditions that favor the activation of the prodrug by PDF and then assaying the sample growth inhibition or microbial death. Alternatively, the sample can be tested for the presence of the byproducts of the reaction of PDF on the substrate. Varying amounts of the substrate is contacted with a microorganism that expresses PDF for an amount of time effective for PDF to release the toxin from the cell, the bacteria is lysed and the analytes are analyzed using methods well known in the art (e.g. High Performance Liquid Chromatography ("HPLC")) to identify the reaction products.

Varying concentrations of the potential agent are contacted with the sample to determine the optimal effective concentration of the agent. Thus, in one aspect, this invention relates to the discovery, and use thereof, of agents that are selective substrates for PDF.

Also provided by this invention are kits containing the prodrugs as described herein and instructions necessary to perform the screen.

The methods of the invention can be practiced in vitro, ex vivo or in vivo. In vivo practice of the invention in an animal such as a rat or mouse provides a convenient animal model system that can be used prior to clinical testing of the therapeutic agent or prodrug. In this system, a potential prodrug will be successful if microbial load is reduced or the symptoms of the infection are ameliorated, each as compared to an untreated, infected animal. It also can be useful to have a separate negative control group of cells or animals which has not been infected, which provides a basis for comparison.

When practiced in vivo, the candidate prodrug is administered or delivered to the animal in effective amounts. As used herein, the term "administering" for in vivo and ex vivo purposes means providing the subject with an effective amount of the candidate prodrug effective to reduce microbial load. In these instances, the agent or prodrug may be administered with a pharmaceutically acceptable carrier. The agents, prodrugs and compositions of the present invention can be used in the manufacture of medicaments and for the treatment of humans and other animals by administration in accordance with conventional procedures, such as an active ingredient in pharmaceutical compositions.

Methods of administering pharmaceutical compositions are well known to those of ordinary skill in the art and include, but are not limited to, microinjection, intravenous or parenteral administration. The compositions are intended for topical, oral, or local administration as well as intravenously, subcutaneously, or intramuscularly. Administration can be effected continuously or intermittently throughout the course of the treatment. Methods of determining the most effective means and dosage of administration are well known to those of skill in the art and will vary with the prodrug used for therapy, the purpose of the therapy, the microorganism being treated, the severity of the infection, and the subject being treated. Single or multiple administrations can be carried out with the dose level and pattern being selected by the treating physician. For example, the compositions can be administered to a subject already suffering from an antibiotic resistant bacterial infection. In this situation, an effective "therapeutic amount" of the composition is administered to prevent continued and to at least partially arrest microbial growth and proliferation and ameliorate the symptoms associated with an infection.

However, the prodrugs can be administered to subjects or individuals susceptible to or at risk of developing an infection. In these embodiments, a "prophylactically effective amount" of the composition is administered to maintain cell viability and function at a level near to the pre-infection level.

Administration in vivo can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents can be found below.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including oral, rectal, nasal, topical (including transdermal, aerosol, buccal and sublingual), vaginal, parenteral (including subcutaneous, intramuscular, intravenous and intradermal) and pulmonary. It will also be appreciated that the preferred route will vary with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient. Desirable blood levels of the agent may be maintained by a continuous infusion to provide a therapeutic amount of the active ingredient within disease tissue. The use of operative combinations is contemplated to provide therapeutic combinations requiring a lower total dosage of each component agent than may be required when each individual therapeutic compound or drug is used alone, thereby reducing adverse effects.

While it is possible for the agent to be administered alone, it is preferable to present it as a pharmaceutical formulation comprising at least one active ingredient, as defined above, together with one or more pharmaceutically acceptable carriers therefor and optionally other therapeutic agents. Each carrier must be "acceptable" in the sense of being compatible with the other ingredients of the formulation and not injurious to the patient.

Formulations include those suitable for oral, rectal, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier that constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound that enhances absorption or penetration of the agent through the skin or other affected areas. Examples of such dermal penetration enhancers include dimethylsulfoxide and related analogues.

The oily phase of the emulsions of this invention may be constituted from known ingredients in an known manner. While this phase may comprise merely an emulsifier (otherwise known as an emulgent), it desirably comprises a mixture of at lease one emulsifier with a fat or an oil or with both a fat and an oil. Preferably, a hydrophilic emulsifier is included together with a lipophilic emulsifier that acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the agent, such carriers as are known in the art to be appropriate.

Formulations suitable for nasal administration, wherein the carrier is a solid, include a coarse powder having a particle size, for example, in the range of about 20 to about 500 microns which is administered as a dry powder or in an inhaler device by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the agent.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of a agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies.

These agents of this invention and the above noted compounds and their derivatives may be used for the preparation of medicaments for use in the methods described herein.

In the clinical use of the prodrug antibiotics will likely follow well established guidelines. Dosage will likely be similar to those already employed for most other antibiotics. It is estimated that a dose of prodrug will be in the range of 100 mg to 1 gm, given once every eight hours, or once a day, for one or two weeks, or until the patient tests negative for infectious organisms.

The following examples are intended to illustrate, but not limit the invention.

EXAMPLE 1

Synthetic Scheme

The following examples of the synthesis of the claimed compounds are meant to be illustrative of the synthesis of the invention and not limit the synthesis of the invention. The synthetic methods, as for example seen below, used to synthesize the compounds are well known to those skilled in the art of organic and medicinal chemistry. Substitutions, modifications or additional steps used in the synthesis of the compounds of the present invention well known to those skilled in the art of organic and medicinal chemistry are anticipated. See, e.g., J. March, ADVANCED ORGANIC CHEMISTRY: REACTIONS, MECHANISMS AND STRUCTURE, $4^{th}$ edition (John Wiley & Sons, NY (1992)).

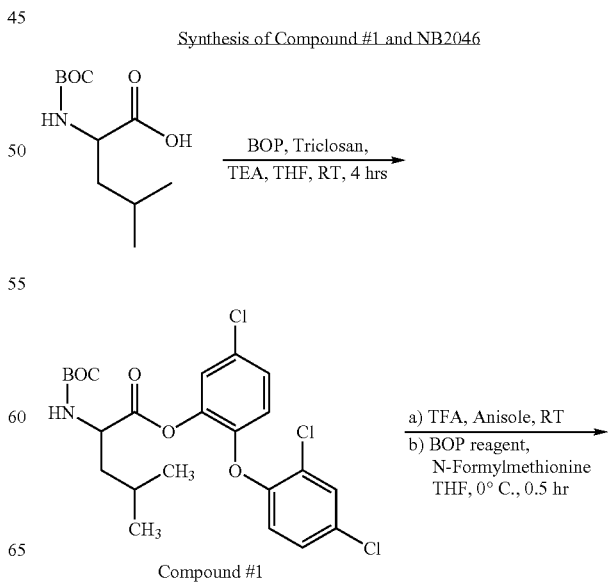

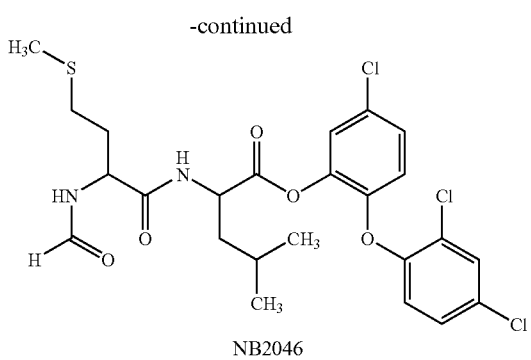

NB2046

In the above synthetic scheme and the following examples, the following acronyms and definitions apply: N-tert-butoxycarbonyl (BOC); benzotriazol-1-yloxytris (dimethylamino)phosphonium hexafluorophosphate (BOP); -triethylamine (TEA); tetrahydrofuran (THF); room temperature (RT); trifluoroacetic acid (TFA); sodium borohydride (NaBH$_4$); phosphorous pentachloride (PCl$_5$); dimethylformamide (DMF); N-methyl-N-trimethylsilyltrifluoroacetamide (MSTFA); diisopropylethylamine (DIEA); and 1,8-diazabicyclo[5.4.0]undec-7-ene (DBU).

Synthesis of Compound 1—Intermediate to Compound NB2046.

A solution of BOC leucine (1.0 g, 4.32 mmol), triclosan (1.25 g, 4.32 mmol), benzotriazol-1-yloxytris(dimethylamino)phosphonium hexafluorophosphate (1.91 g, 4.32 mmol), and triethylamine (1.33 g, 12.9 mmol) in anhydrous THF (25 ml) was stirred at 0° C. under argon atmosphere for 4 hours. Water (20 ml) was added and the reaction mixture was extracted with ethylacetate (2×30 ml). Combined organic layers were washed with water, brine, and dried over Na$_2$SO$_4$. Evaporation of the solvent and purification using silica gel column chromatography with 2% ethylacetate in hexane as eluant provided compound 1 as a colorless gum (1.66 g, 75%).

$^1$H NMR (CDCl$_3$, 500 MHz): 0.91 (d, 2H, J=Hz), 1.43 (s, 9H), 1.51–1.60 (m, 2H), 1.69–1.73 (m, 1H), 4.43–4.48 (m, 1H), 4.83 (d, 1H, J=Hz), 6.80 (d, 1H, J=Hz), 6.86 (d, 1H, J=Hz), 7.14–7.26 (m, 2H), 7.26 (s, 1H) 7.43 (d, 1H, J=Hz).

Synthesis of Compound NB2046.

A solution of compound-1 (0.25 g, 0.5 mmol), in anhydrous anisole (0.055 g, 0.5 mmol), was cooled to 0° C. and TFA (0.56 g, 5.0 mmol) was added slowly over 15 minutes. The ice bath was removed and stirring continued for another 3 hours. All the volatiles were then removed under reduced pressure to get a gum. Anhydrous THF was added and cooled to 0° C. under argon atmosphere. Benzotriazol-1-yloxytris(dimethylamino)phosphonium hexafluorophosphate (0.25 g, 0.57 mmol), N-formyl methionine (0.1 g, 0.57 mmol), and triethylamine (0.21 g, 2.1 mmol) were added. Thin layer chromatography showed the completion of reaction after 0.5 hour at 0° C. The reaction was washed with water, brine, and dried Na$_2$SO$_4$. Purification on silica gel column chromatography provided NB2046 as colorless thick gum.

$^1$H NMR (CDCl$_3$, 500 MHz): 0.88 (d, 3H, J=Hz), 0.91 (d, J=Hz), 1.50–1.56 (m, 1H), 1.60–1.71 (m, 2H), 1.95–2.02 (m, 1H), 2.09 (s, 3H), 2.50 (m, 1H), 2.58 (m, 1H), 4.65–4.70(m, 1H), 4.74 (q, 1H, J=Hz), 6.48 (d, 1H), 6.78–6.85 (m, 2H), 7.15–7.25 (m, 3H), 7.44 (s, 1H), 8.17 (s, 1H).

General Synthetic Scheme of Intermediates (Compounds 3 and 4) to Compounds NB3024, NB3057, NB3068 and NB3103:

The following examples of the synthesis of the claimed compounds are meant to be illustrative of the synthesis of the invention and not limit the synthesis of the invention. The synthetic methods, as for example seen below, used to synthesize the compounds are well known to those skilled in the art of organic and medicinal chemistry. Substitutions, modifications or additional steps used in the synthesis of the compounds of the present invention well known to those skilled in the art of organic and medicinal chemistry are anticipated. See, e.g., J. March, ADVANCED ORGANIC CHEMISTRY: REACTIONS, MECHANISMS AND STRUCTURE, 4$^{th}$ edition (John Wiley & Sons, NY (1992)).

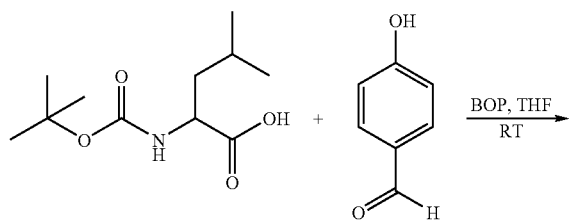

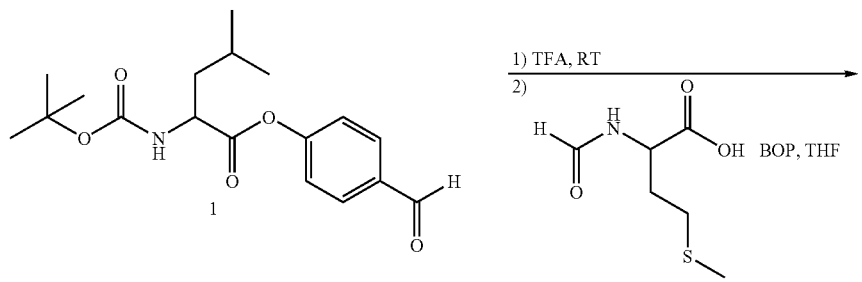

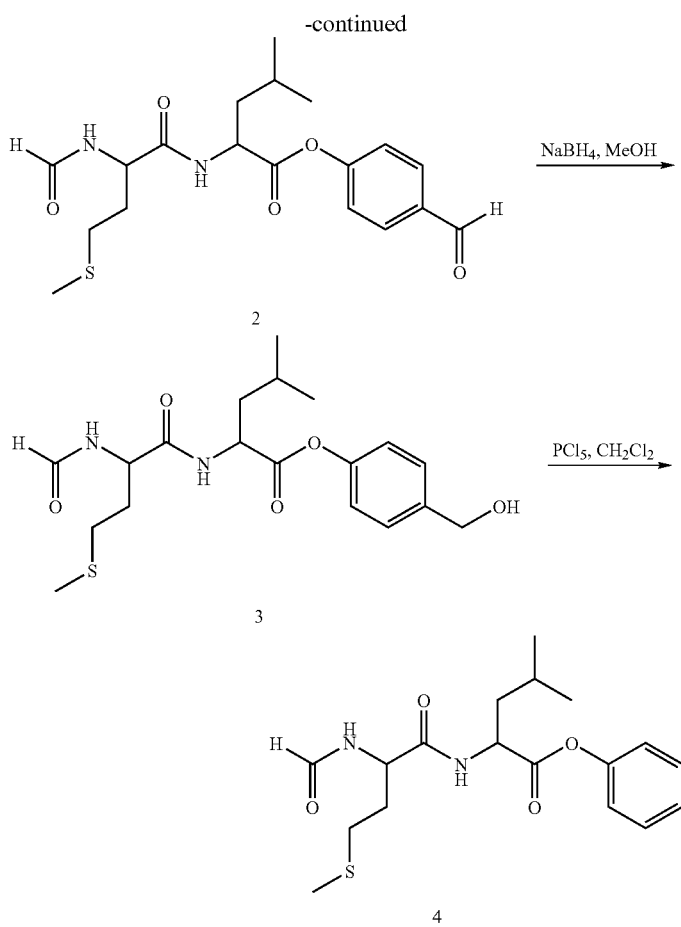

Detailed Description of Synthetic Scheme of Intermediates

Synthesis of 2-tert-Butoxycarbonylamino-4-methyl-pentanoic acid 4-formyl-phenyl ester (Compound 1)

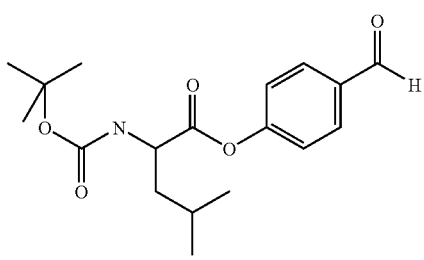

BOP (13.0 mmol) was added to a solution of N-tert-butyloxycarbonyl-L-leucine (10.9 mmol) and 4-hydroxy-benzaldehyde (13.0 mmol) in dry DMF (12 mL), and stirred to dissolve. N,N-Diisopropylethylamine (43.0 mmol) and 4-dimethylaminopyridine (1 mmol) were added with stirring. The resulting solution was stirred for 2.5 hours. The reaction mixture was covered with dichloromethane (100 mL) and washed with water, saturated aqueous sodium bicarbonate, and saturated brine. The dichloromethane was dried over anhydrous sodium sulfate, filtered, and concentrated under vacuum. The resulting red oil was purified by column chromatography on silica gel with dichloromethane as an eluant.

$^1$H NMR (CDCl$_3$, 500 MHz): 1.01–1.02 (m, 6H), 1.46 (s, 9H), 1.64–1.68 (m, 1H), 1.76–1.83 (m, 2H), 4.52–4.54 (m, 1H), 4.92–4.94 (d, 2H, J=7.6 Hz), 7.28–7.29 (d, 2H, J=8.48 Hz), 7.91–7.93 (d, 2H, J=8.48 Hz), 9.99 (s, 1H).

Synthesis of 2-(2-Formylamino-4-methylsulfanyl-butyrylamino)-4-methyl-pentanoic acid 4-formyl-phenyl ester (Compound 2)

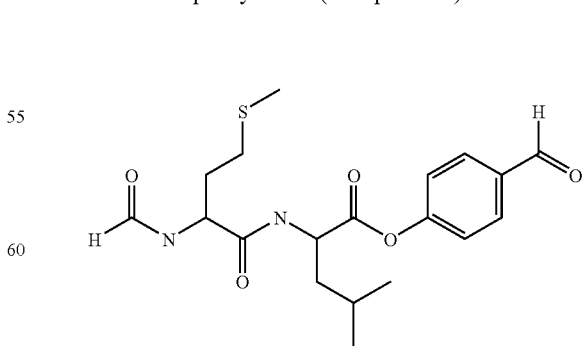

A solution of compound 1 (10 mmol) in TFA (100 mmol) was stirred at RT for 1 hour under inert atmosphere. All the volatiles were then removed under reduced pressure and the residue was dissolved in THF (10 mL). N-formyl-L-methionine (10 mmol), BOP (13.0 mmol), followed by N,N-Diisopropylethylamine (30.0 mmol) and 4-dimethylaminopyridine (1 mmol) were added with stirring. After the completion of reaction, THF was removed under reduced pressure and dichloromethane (25 ml) was added. The reaction mixture was washed with water, saturated aqueous sodium bicarbonate, and saturated brine. The dichloromethane was dried over anhydrous sodium sulfate, filtered, and concentrated under vacuum. The resulting think gum was purified by column chromatography on silica gel with 0 to 5% methanol in dichloromethane as an eluant.

Synthesis of 2-(2-formylamino-4-methylsulfanyl-butyrylamino)-4-methyl-pentanoic acid 4-hydroxymethyl-phenyl ester (Compound 3)

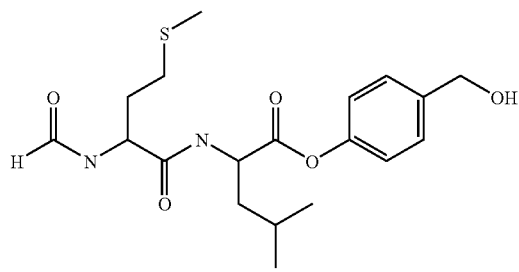

To synthesize the above compound, a solution of compound 2 (1.0 mmol) in methanol (10 mL) was cooled to 0° C. and a solution of NaB$_4$ (0.25 mmol) in methanol was slowly added. After 5 min 0.1 N HCl was added and the volatiles were removed at reduced pressure. The resultant mixture was partitioned between water and ethyl acetate (10 mL). Separated ethyl acetate layer was washed with brine and dried over Na$_2$SO$_4$. Removal of volatiles provided compound 3 in quantitative yield as light yellow gum.

$^1$H NMR (CDCl$_3$, 500 MHz) 0.99–1.03 (m, 6H), 1.71–1.87 (m, 3H), 2.02–2.15 (m, 2H), 2.11 (s, 3H), 2.53–2.66 (m, 2H), 4.68 (s, 2H), 4.76–4.79 (m, 2H), 6.46–6.47 (m, 1H), 6.70–6.74 (m, 1H), 7.06–7.08 (m, 2H), 7.36–7.39 (m, 2H), 8.19 (s, 1H).

Synthesis of 2-(2-Formylamino-4-methylsulfanyl-butyrylamino)-4-methyl-pentanoic acid 4-chloromethyl-phenyl ester (Compound 4)

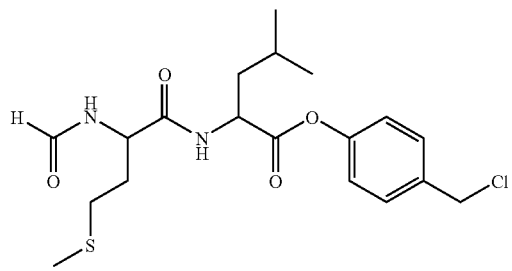

A solution of compound 3 (0.2 grams, 0.55 mmol) in anhydrous dichloromethane was cooled in an ice bath and PCl$_5$ (0.11 grams, 0.55 mmol) was added under argon atmosphere. After the completion of the reaction aqueous NaHCO$_3$ was added and stirred for 10 min. Organic layer was separated, washed with water, brine and dried (Na$_2$SO$_4$). Evaporation of volatiles provided the title compound, which was used for the next reaction without further purification.

$^1$H NMR (CDCl$_3$, 500 MHz): 1.00–1.03 (m, 6H), 1.72–1.86 (m, 3H), 2.02–2.15 (m, 2H), 2.1 (s, 3H), 2.53–2.66 (m, 2H), 4.57 (s, 2H), 4.75–4.81 (m, 2H), 6.46–6.47 (m, 1H), 6.73–6.77 (m, 1H), 7.07–7.10 (m, 2H), 7.38–7.41 (m, 2H), 8.20 (s, 1H).

Synthetic Scheme of Synthesis of Compound NB3024

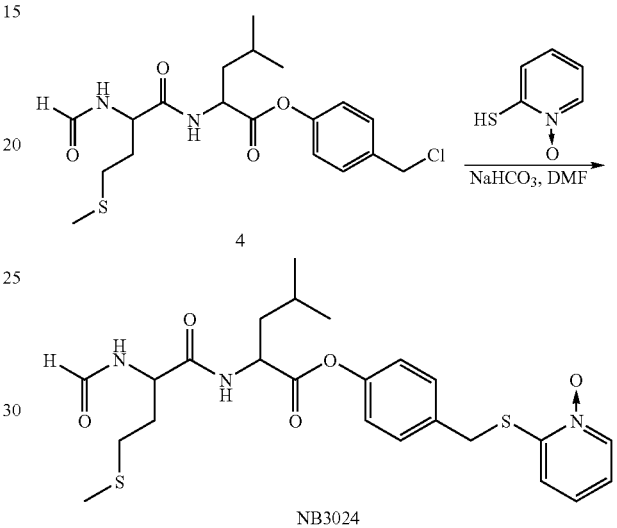

Detailed Description of Synthesis of Compound NB3024

2-(2-Formylamino-4-methylsulfanyl-butyrylamino)-4-methyl-pentanoic acid 4-(1-hydroxy-1,2-dihydro-pyridin-2-ylsulfanylmethyl)-phenyl ester (NB3024)

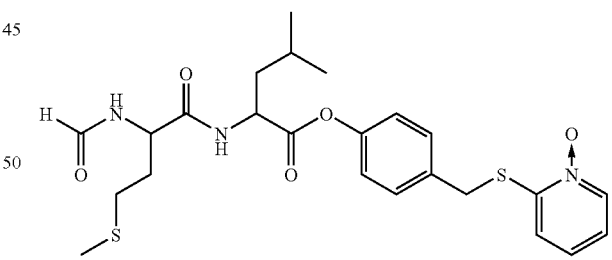

To a solution of compound 4 (1.0 mmol) in anhydrous DMF (2 mL) sodium bicarbonate (2.5 mmol) and pyrithione (1.0 mmol) was added and stirred under inert atmosphere for 1 hr. Reaction mixture was then filtered and DMF was removed under reduced pressure. Passing it through a short silica gel column purified the crude product.

$^1$H NMR (CDCl$_3$, 500 MHz): 0.98–1.02 (m, 6H), 1.71–1.84 (m, 3H), 2.02–2.21 (m, 2H), 2.14 (s, 3H), 2.60–2.66 (m, 2H), 4.15 (s, 2H), 4.75–4.78 (m, 2H), 6.48–6.50 (m, 1H), 6.70–6.74 (m, 1H), 7.06–7.08 (m, 3H), 7.12 (d, 1H, J=7.7 Hz), 7.21–7.24 (m, 1H) 7.36–7.39 (m, 2H), 8.19 (s, 1H), 8.26 (d, 1H, J=6.36 Hz).

Synthetic Scheme of Synthesis of Compound NB3057

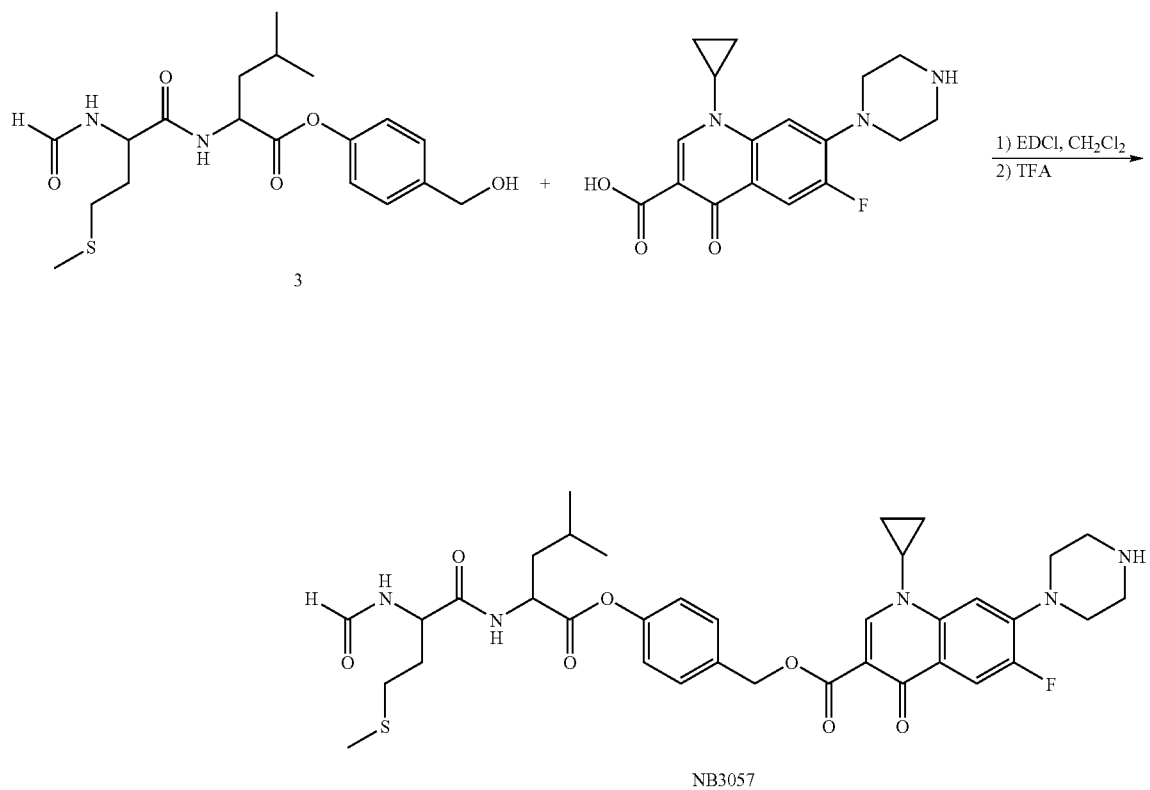

NB3057

Detailed Description of Synthesis of Compound NB3057

1-Cyclopropyl-6-fluoro-4-oxo-7-piperazin-1-yl-1,4-dihydro-quinoline-3-carboxylic acid 4-[2-(2-formylamino-4-methylsulfanyl-butyrylamino)-4-methyl-pentanoyloxy]-benzylester

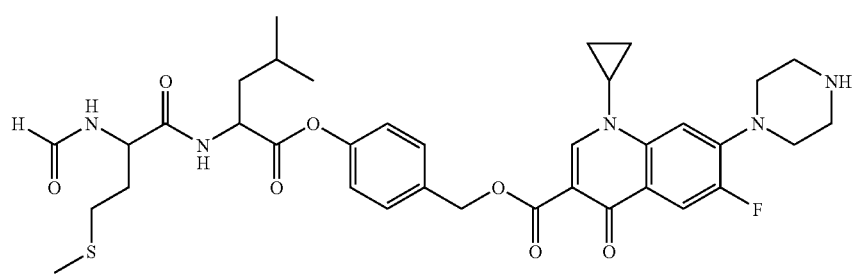

To a solution of compound 3 (1.0 mmol) and BOC-ciprofloxacin (1.0 mmol) in anhydrous dichloromethane (10 mL), EDCI (2.0 mmol) was added. After 48 hrs at RT the crude reaction mixture was loaded on a silica gel column and the product was eluted with 5% methanol in dichloromethane.

$^1$H NMR(DMSO-d6), 500 MHz): 0.89–0.91 (m, 3H0, 0.94–0.96 (m, 3H), 1.10–1.12 (m, 2H), 1.25–1.26 (m, 2H), 1.70–1.75 (m, 4H), 2.02–2.15 (m, 2H), 2.11 (s, 3H), 3.44 (brs, 4H), 3.78 (brs, 4H), 3.42–3.44 (m, 1H), 4.50–4.55 (m, 2H), 5.27 (s, 2H), 7.08–7.10 (m, 2H), 7.47–7.49 (m, 1H), 7.53–7.55 (m, 1H), 7.85 (d, 1H, J=12 HZ), 8.02 (s, 1H), 8.35(t, 1H, J=12.64 Hz), 8.50 (s, 1H), 8.62–8.68 (m, 1H), 8.79 (s, 2H).

Synthetic Scheme of Synthesis of Compound NB3068

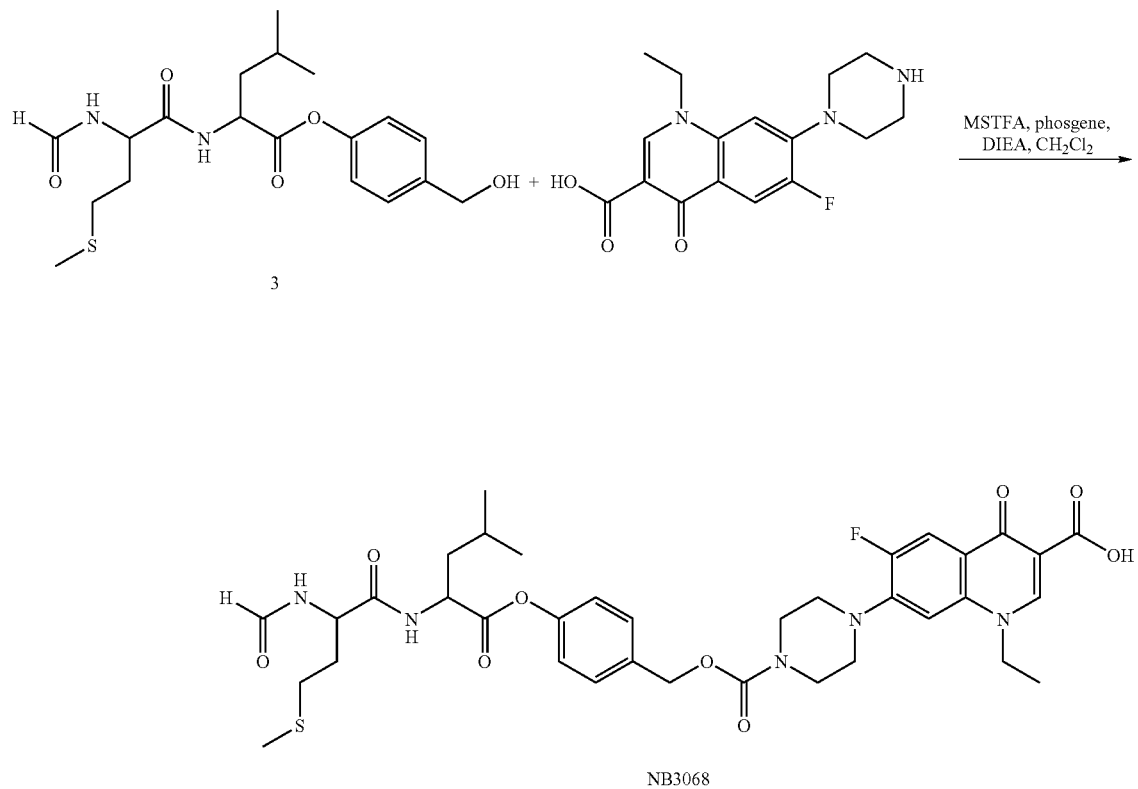

NB3068

Detailed Description of Synthesis of NB3068

1-Ethyl-6-fluoro-7-(4-{4-[2-(2-formylamino-4-methylsulfanyl-butyrylamino)-4-methyl-pentanoyloxy]-benzyloxycarbonyl}-piperazin-1yl)-4-oxo-1,4-dihydro-qiuinoline-3-carboxylic acid (NB3068)

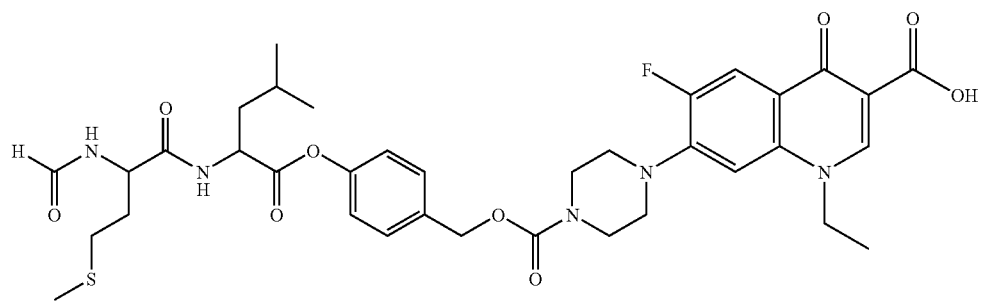

To a mixture of norfloxacin (84 mg, 0.26 mmol) in anhydrous dichloromethane (2 mL) MSTFA (100 mg, 0.5 mmol) was added and stirred for 30 min at RT. In the mean time a solution of compound 3 (140 mg, 0.35 mmol) and DIEA (70 mg, 0.4 mmol) was taken in another flask and phosgene (40 mg, 0.4 mmol) was added at 0° C. This solution was then added to the solution of norfloxacin and stirred at room temperature for 1 hour. The reaction mixture was washed with 0.1 N HCl and dried over $Na_2SO_4$. Volatiles were removed and ether (5 mL) was added. The precipitated product was then filtered.

$^1$H NMR (CDCl$_3$, 500 MHz): 0.99–1.03 (m, 6H), 1.55 (m, 3H), 1.71–1.87 (m, 3H), 2.02–2.15 (m, 2H), 2.11 (s, 3H), 2.53–2.66 (m, 2H), 3.27 (brs, 4H), 3.78 (brs, 4H), 4.30 (q, 2H, J=7.19, 14.44 Hz), 4.76–4.80 (m, 2H), 5.15 (s, 2H), 6.46–6.47 (m, 1H), 6.71–6.72 (m, 1H), 6.83 (d, 1H, J=6.87 Hz), 7.08–7.10 (m, 2H), 7.38–7.41 (m, 2H), 8.10 (d, 1H, J=12.64 Hz), 8.21 (s, 1H), 8.68 (s, 1H).

Synthetic Scheme of Synthesis of Compound NB3103

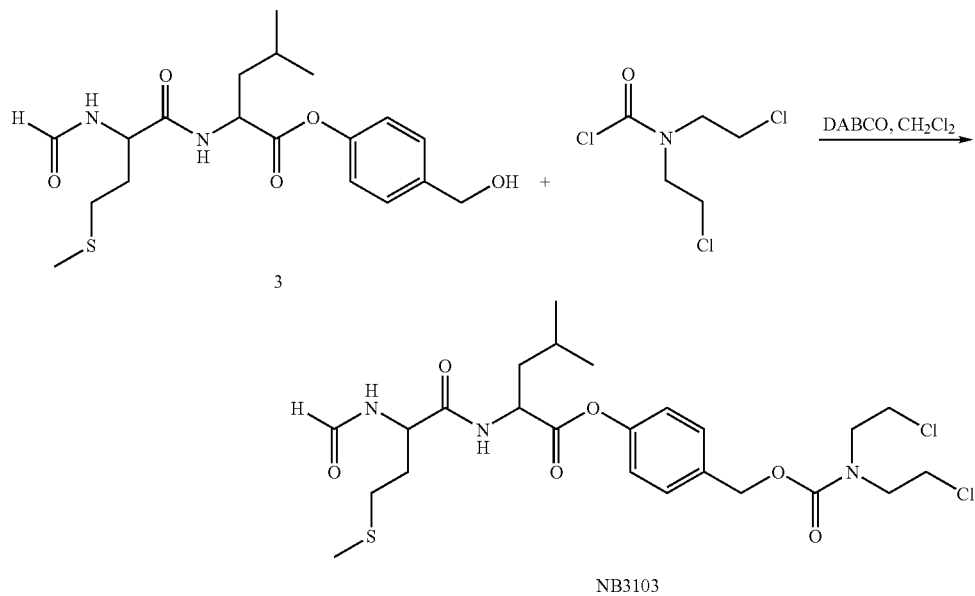

NB3103

Detailed Description for Synthesis of NB3103

2-(2-Formylamino-4-methylsulfanyl-butyrylamino)-4-methyl-pentanoic acid 4-{[bis-(2-chloro-ethyl)-carbamoyloxy]-methyl}-phenyl ester (NB3103)

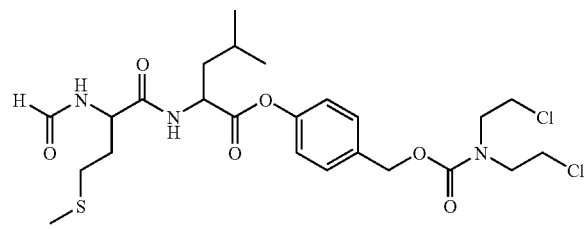

To a solution of compound 3 in anhydrous dichloromethane bis-dichloroethane carbamoyl chloride and DBU were added at room temperature. After 15 minutes the reaction mixture was washed with water (10 mL) and purified on silica gel column.

$^1$H NMR(CDCl$_3$, 500 MHz): 0.99–1.03 (m, 6H), 1.71–1.84 (m, 3H), 2.02–2.21 (m, 2H), 2.11 (s, 3H), 2.64–2.67 (m, 2H), 3.57–3.77 (m, 8H), 4.76–4.81 (m, 2H), 5.13 (s, 2H), 6.42–6.44 (m, 1H), 6.70 (d, 1H, J=8.1 Hz), 7.08–7.13 (m, 2H), 7.35–7.38 (m, 2H) 8.20 (s, 1H).

EXAMPLE 2

Susceptibility Testing

The NCCLS (National Committee for Clinical Laboratory Standards), method to determine MIC's of antimicrobial compounds is modified for high-throughput screening. All stocks of tested compounds are prepared in either water or in DMSO depending on solubility. At the highest concentration, DMSO content should not exceed 0.5%. Briefly, twenty 2-fold serial dilutions of test compounds from the highest concentration are made in a 384-well microtiter plate. Each well is inoculated with testing bacteria in broth to a final concentration of approximately 1–1.5×10$^6$ cells/ml. Bacterial growth is determined by the increase of optical density at 600 nm using a microplate reader (Tecan SpectraFluor Plus). The MIC is defined as the lowest concentration at which bacterial growth (equivalent to visible growth) was inhibited after 16 to 18 hours of incubation at the appropriate temperature required for the bacteria growth. Results for NB2046 are shown in Table 3 and Table 4.

TABLE 3

| | | MIC (µg/ml) | |
|---|---|---|---|
| Organism | ATCC# | Exp. #1 | Exp. #2 |
| S. aureus | 700260 | ≦0.125 | ≦0.125 |
| S. aureus | 700698 | ≦0.125 | ≦0.125 |
| S. aureus | 700699 | 16 | 8 |
| S. aureus | 13301 | ≦0.125 | ≦0.125 |
| S. aureus | 11632 | ≦0.125 | ≦0.125 |
| S. aureus | 14154 | ≦0.125 | ≦0.125 |
| S. aureus | 700787 | ≦0.125 | ≦0.125 |
| S. aureus | 700788 | ≦0.125 | ≦0.125 |
| S. aureus | 700789 | ≦0.125 | ≦0.125 |
| S. aureus | 43300 | ≦0.125 | ≦0.125 |
| S. aureus | 33591 | ≦0.125 | ≦0.125 |
| S. aureus | 33592 | ≦0.125 | ≦0.125 |
| S. aureus | 33593 | ≦0.125 | ≦0.125 |
| S. epidermidis | 27626 | ≦0.125 | ≦0.125 |
| S. epidermidis | 700565 | 2 | 2 |
| S. epidermidis | 700566 | ≦0.125 | ≦0.125 |
| S. epidermidis | 700578 | 0.5 | 0.25 |
| S. epidermidis | 700583 | ≦0.125 | ≦0.125 |
| K. pneumoniae | 51503 | 8 | 8 |
| K. pneumoniae | 51504 | 1 | 2 |
| K. pneumoniae | 700721 | 2 | 2 |
| E. aerogenes | 29751 | 2 | 1 |
| E. cloacae | 23355 | 0.5 | 0.5 |
| E. aerogenes | 29009 | 0.25 | ≦0.125 |
| E. aerogenes | 13048 | 1 | 1 |
| E. aerogenes | 35028 | 4 | 2 |

TABLE 3-continued

| | | MIC (μg/ml) | |
|---|---|---|---|
| Organism | ATCC# | Exp. #1 | Exp. #2 |
| M. catarrhalis | 49265 | ≦0.125 | ≦0.125 |
| M. catarrhalis | 51584 | ≦0.125 | ≦0.125 |
| M. catarrhalis | 43627 | ≦0.125 | ≦0.125 |
| M. catarrhalis | 43628 | ≦0.125 | ≦0.125 |

TABLE 4

| | | MIC (μg/ml) | |
|---|---|---|---|
| Organism | ATCC# | Exp. #1 | Exp. #2 |
| E. coli | | 16 | 16 |
| E. coli/Tem-1 | | 16 | 16 |
| MSSA | 700260 | ≦0.125 | 4 |
| MRSA | 700699 | 32 | 32 |
| MSSA | 33594 | ≦0.125 | ≦0.125 |
| MSSA | 11632 | 32 | 16 |
| E. faecalis | 49757 | 64 | 32 |
| E. faecalis | 700802 | 32 | 32 |
| E. fecium | | | |
| E. fecium | | | |
| E. aerogenes | 35028 | 32 | 16 |
| E. cloacae | 23355 | 16 | 1 |
| K. pneumoniae | 700721 | 4 | 8 |
| K. pneumoniae | 51503 | 4 | 8 |
| H. influenzae | 33533 | 64 | ≧64 |
| H. influenzae | 43334 | | |
| P. aeruginosa | 21726 | >64 | ≧64 |
| P. aeruginosa | 29872 | >64 | ≧64 |

E. coli/TEM—E. coli expressing TEM-1 beta-lactamase; MRSA—Methicillin Resistant S. Aureus; MSSA—Methicillin Sensitive S. Aureus Mammalian cells were treated with NB2046 as described above. The compound is not toxic to mammalian cells ($IC_{50}$ of about 30 μM) after 16 hours of exposure.

Using the assay provided above, the potency of NB2046 was compared to triclosan. Results are shown in Table 5.

TABLE 5

| MSSA (ATCC ##) | NB2046 MIC, μg/ml | Triclosan MIC, μg/ml |
|---|---|---|
| 700260 | 0.000031 | 0.000244 |
| 13301 | 0.000015 | 0.000488 |
| 11632 | 0.000977 | 0.001953 |
| 14154 | 0.000977 | 0.001953 |
| 33592 | 0.000488 | 0.003906 |
| 43300 | 0.000977 | 0.001953 |
| 700698 | 0.003906 | 0.003906 |
| 700699 | ≧4 | ≧4 |
| 700787 | 0.007813 | 0.001953 |
| 700788 | 0.062500 | 0.031250 |
| 700789 | 0.015630 | 0.015630 |
| 33591 | 0.015630 | 0.007813 |
| 33593 | 0.000488 | 0.000977 |

EXAMPLE 3

In a seperate experiment, cell-free reaction of PDF ECTA compounds has been studied using PDF purified from PDF-overexpressing E. coli following a procedure described in Ragusa S., et al. (2000) and Wei, et al. (2000b). NB3068 conversion was used as an example of a PDF ECTA reaction catalyzed by purified PDF. It was carried out in 50 mM HEPES buffer, pH 7.5 at room temperature. NB3068 concentrations were in the range of 2–250 μM, and the concentration of the enzyme in the reaction mixture was 25 nM. The conversion was monitored by direct injection of the reaction mixture onto an HPLC column (Adsorbosphere HS, C18, 5 μm, 4.6 mm×150 mm, Alltech). Both the decrease of NB3068 concentration and the increase of ciprofloxacin concentration were monitored, and initial rates of the reactions were calculated. Kinetic parameters of the reaction were determined fitting the data to the Michaelis-Menten equation. The dependence of the rate of the reaction on the substrate concentration is given in FIG. 2. From this dependence the following kinetic parameters of PDF-catalyzed NB3068 reaction were obtained: $k_{cat}=2.07\pm0.14$ s$^{-1}$, $K_m=125\pm17$ μM, and $k_{cat}/K_m=1.7\times10^4$ M$^{-1}$s$^{-1}$.

Alternatively, a series of PDF ECTA compounds at a concentration of 20–100 μM in 50 mM HEPES buffer, pH 7.5 have been contacted with purified PDF at a concentration of 25 nM, and the consumption of the compound was followed. The consumption of the compound was fit to an exponential equation. Under the conditions of the substrate concentration being less or comparable to $K_m$ the exponential constant can be approximated as $(k_{cat}/K_m)\times[E]$. A relative catalytic efficiency parameter ($k_{cat}/K_m$) for a number of substrates has been determined; the $k_{cat}/K_m$ value for NB3068 was assigned a value of 1 (see Table 6).

TABLE 6

Properties of PDF ECTA compounds

| | | $t_{1/2}$ (hrs)* | | | $t_{1/2}$ (min)* | |
| | Catalytic | | | | Mouse | Human |
| Ref. No. | Efficiency | PBS | HEPES | Broth | Plasma | Plasma |
|---|---|---|---|---|---|---|
| NB3024 | 1.47 | >12 (81%) | >12 (88%) | >12 (82%) | n/d | n/d |
| NB3057 | 1.05 | >12 (82%) | >12 (81%) | 10 | 1.4 | <0.5 |
| NB3068 | 1 | >12 (75%) | >12 (70%) | >12 (70%) | 0.6 | 4.1 |
| NB3103 | 0.84 | >12 (96%) | >12 (95%) | >12 (95%) | n/d | n/d |

Figure 3:
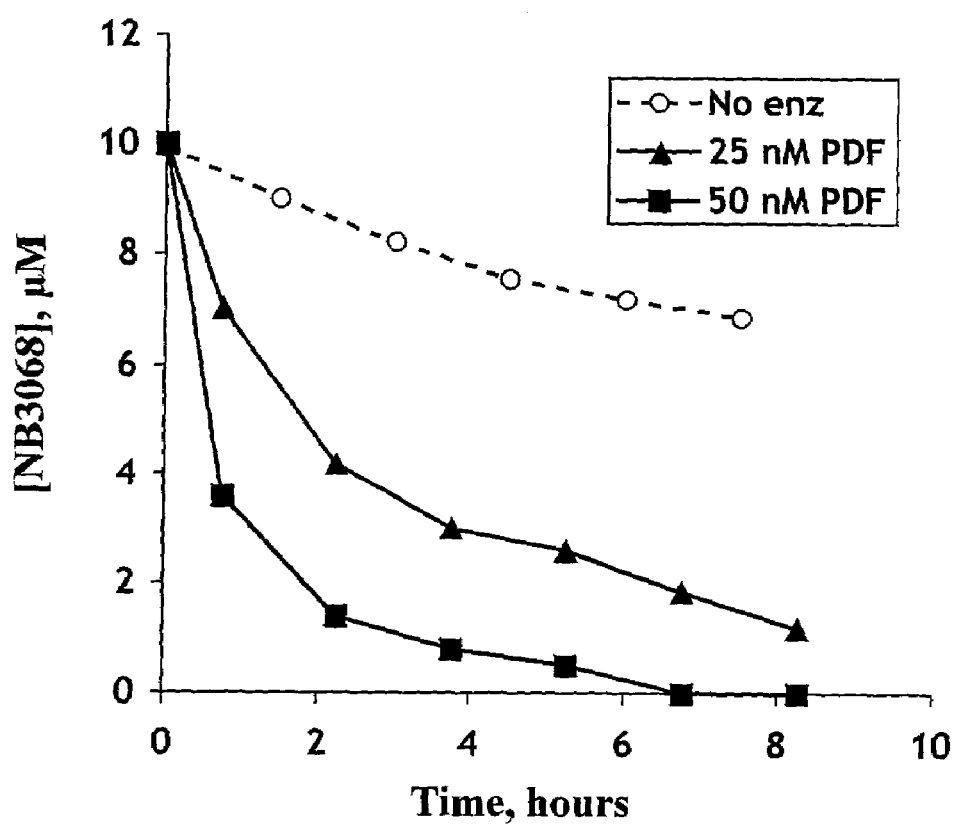
FIG. 3 shows time dependence of the concentration of NB3068 in the reaction catalyzed by different concentrations of purified PDF.
Figure 4:
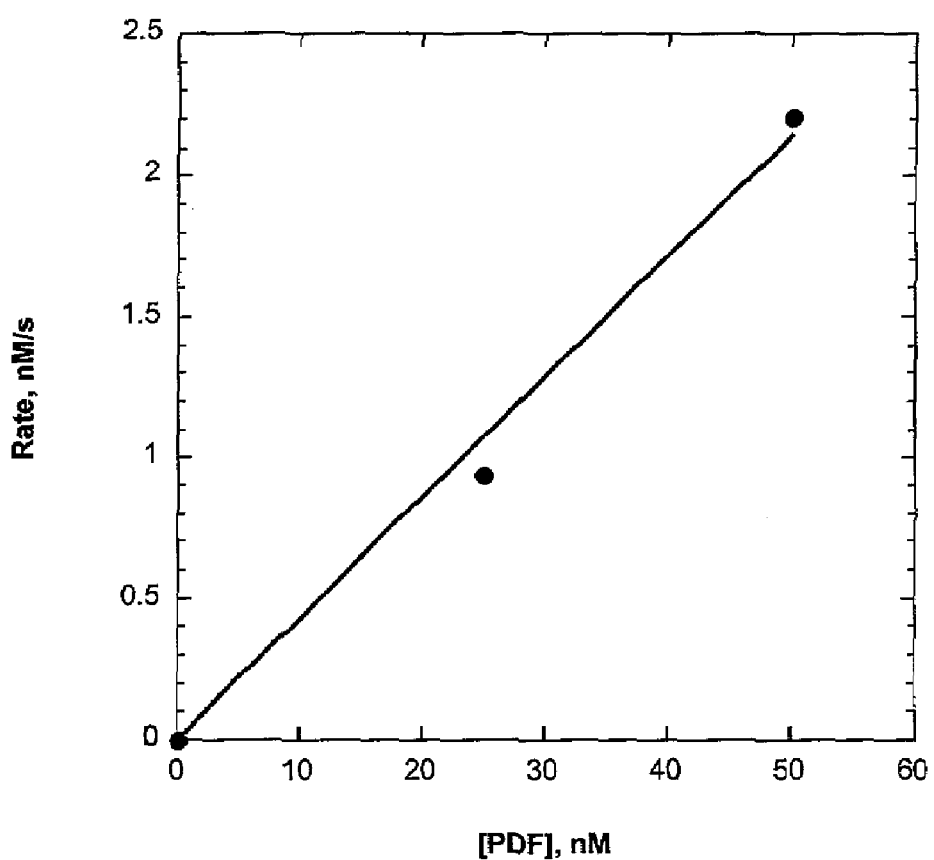
FIG. 4 shows dependence of the initial rate of the NB3068 reaction catalyzed by purified PDF on PDF concentration.

*$t_{1/2}$—half-life (in parenthesis - percent of the compound remaining after 6 hours
n/d—not determined To confirm the role of PDF in catalyzing NB3068 transformation the rate of the reaction at different enzyme concentrations was determined (FIGS. 3 and 4**). As can been seen the rate of the reaction is proportional to the enzyme concentration.

Figure 5:
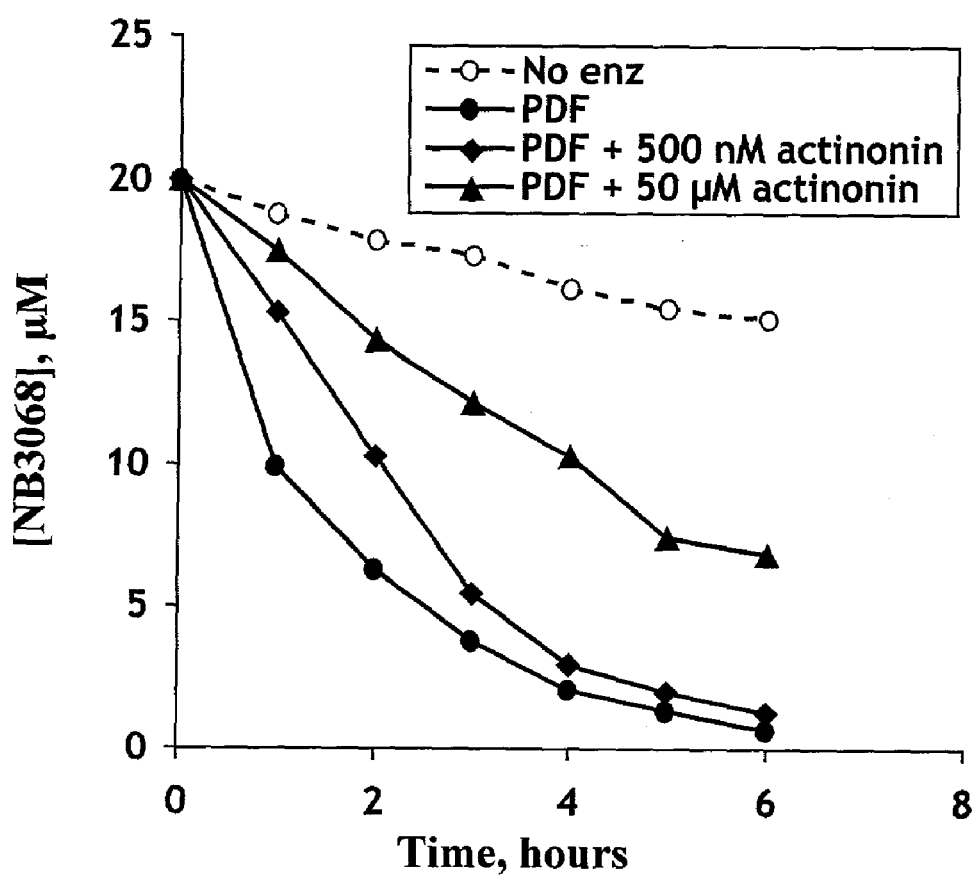
FIG. 5 shows time dependence of the concentration of NB3068 in the reaction catalyzed by purified PDF at different concentrations of actinonin.

To further confirm the role of PDF NB3068 reaction catalyzed by purified PDF was studied in the presence of actinonin—PDF specific inhibitor. As can be seen from FIG. 5 addition of actinonin to the reaction mixture slows down the reaction in dose dependent manner.

EXAMPLE 4

Stability

Stability of PDF ECTA compounds was determined in different media: PBS, pH 7.4 (Gibco Life Technologies), 50 mM HEPES buffer (Sigma), pH 7.5, Mueller Hinton broth (Becton Dickinson), mouse and human plasma (Sigma). Dependence of a compound concentration on time was fit to an exponential equation $c=c_o\times exp(-k\times t)$} where c is the running concentration of the compound, $c_o$ is its initial concentration and t is time. The compound half-life was determined as $t_{1/2}=0.693/k$.

EXAMPLE 5

Susceptibility Testing

The NCCLS (National Committee for Clinical Laboratory Standards) method was used to determine MIC's of antimicrobial compounds. All stocks of tested compounds were prepared in either water or DMSO based on the solubility. At the highest concentration of the tested compound DMSO content should not exceed 0.5%. Briefly 2-fold serial dilutions of test compounds from the highest concentration were made in a 96-well microtiter plate. Each well was inoculated with testing bacteria in broth to a final concentration of approximately $5\times10^5$ CFU/ml. Bacterial growth was monitored by the increase of optical density at 600 nm using a microplate reader (Tecan SpectraFluor Plus). The MIC was defined as the lowest concentration at which bacteria growth (equivalent to visible growth) was inhibited after 18 hours of incubation at 35° C. MIC values obtained for each compound are given in Table 7.

TABLE 7

MIC values for PDF ECTA compounds

| Organisms | ATCC ## | NB3024 | NB3057 | NB3068 | NB3103 |
|---|---|---|---|---|---|
| E. coli | 25922 | 16 | 0.0625 | <0.004 | >128 |
| E. faecalis | 29212 | 32 | 4 | 2 | >128 |
| S. aureus (MS) | 29213 | 8 | 0.125 | 2 | >128 |
| S. aureus (MR) | 33591 | n/d* | 0.5 | n/d* | n/d* |
| P. aeruginosa | 27853 | 128 | 2 | 0.5 | >128 |

*n/d—not determined

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

REFERENCES

Apfel, C. et al. (2000) *J. Med. Chem.* 43:2324–2331.
Apfel et al. (2001a) *Anti. Agents and Chemo.* 45(4):1053–1057.
Apfel et al. (2001b) *Anti. Agents and Chemo.* 45(4):1058–1064.
Becker, A. et al. (1998) *Nat. Struct. Biol.* 5(12): 1053–8.
Chan, M. K. et al. (1997) *Biochemistry* 36(45):13904–9.
Chen, D. Z. et al. (2000) *Biochemistry* 39(6): 1256–62.
Clements, J. M. et al. (2001) *Anti. Agents and Chemo.* 45(2):563–570.
de Groot, F. M. H. et al. (2000) *J. Med. Chem.* 43:3093–3102.
Durand et al. (1999) *Arch. Bio. And Biophysics.* 367(2): 297–302.
Giglione, C. et al. (2000a) *Mol. Microbiol.* 36:1197205.
Giglione, C. et al. (2000b) *EMBO J.* 19(21):5916–5929.
Hao, B. et al. (1999) *Biochemistry* 38(15):4712–9.
Hu, Y. J. et al. (1998) *Bioorg Med Chem Lett.* 8(18): 2479–82.
Huntington, K. M. et al. (2000) *Biochemistry* 39(15):4543–51.
Jayasekera, M. M. et al. (2000) *Arch. Biochm. Biophys.* 381(2):313–316.
Meinnel, T. (1999) *Pathol. Biol.* 47:780–783.
Meinnel, T. et al. (1993) *Biochimie.* 75(12):1061–75. Review.
Nelson, D. L. et al. (2000) *Principles of Biochemistry.* 2000, ed. Lehninger,
Ragusa S., et al. (2000) *J. Mol. Biol.,* 280, 551–523.
Rajagopalan, P. T. et al. (1997) *Biochemistry* 36(45):13910–8.
Rajagopalan, P. T. et al. (1998) *Biol Chem.* 273(35):22305–10.
Wei Y. et al. (1997) *Anal Biochem.* 250(1):29–34.
Wei, Y. et al. (2000) *J Comb Chem.* 2(6):650–7.
Wei, Y. et al. (2000b) *Bioorg Med Chem Lett.* 10(10): 1073–6.

We claim:

1. A compound having the structure:

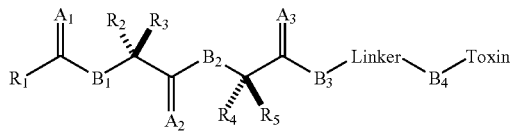

wherein $R_1$, $R_2$ are each hydrogen and $R_4$, and $R_5$ are independently the same or different and are selected from the group consisting of hydrogen, a substituted or unsubstituted $C_5$–$C_{14}$ aryl group and a substituted or unsubstituted, saturated or unsaturated $C_1$–$C_6$ alkyl group;

wherein $R_3$ is selected from the group consisting of a substituted or unsubstituted aryl group and a substituted or unsubstituted, saturated or unsaturated $C_1$–$C_6$ alkyl group and —$CH_2$—$CH_2$—X—$CH_3$, wherein X is selected from the group consisting of —O—, —S—, —NH—, —$NR_6$—, and —$CH_2$—; where $R_6$ is a lower alkyl;

wherein $A_1$ and $A_3$ are independently the same or different and are selected from the group consisting of =O, =S, =NH, =N—OH, or =N—$R_7$, where $R_7$ is hydrogen or a $C_1$–$C_6$ alkyl;

wherein $A_2$, is absent or selected from the group consisting of =O, =S; =NH, =N—OH, =N—$R_8$, or —C($R_9$)($R_{10}$)—, wherein $R_8$, $R_9$, and $R_{10}$ are independently the same or different and are selected from the group consisting of hydrogen or a $C_1$–$C_6$ alkyl;

wherein $B_1$ is selected from the group consisting of —O—, —S—, —NH— or —N($R_{11}$)—, wherein $R_{11}$ is selected from the group consisting of hydrogen and a $C_1$–$C_6$ alkyl;

wherein $B_2$ is absent or is selected from the group consisting of —O—, —S—, —N($R_{12}$), or —C($R_{13}$)($R_{14}$)—, where $R_{12}$, $R_{13}$, and $R_{14}$ are independently the same or different and are selected from the group consisting of hydrogen or a substituted or unsubstituted, saturated or unsaturated alkyl;

wherein the fragment —$B_2$—C($R_4$)($R_5$)—C(=$A_3$)— in its entirety is an naturally occurring amino acid, analog, derivative or peptidomimetic thereof;

wherein $B_3$ is absent or is selected from the group consisting of —O—, —S—, or —NH—, or —N($R_{15}$)—, wherein $R_{15}$ is selected from the group consisting of hydrogen and a $C_1$–$C_6$ alkyl;

wherein $B_4$ is absent or is selected from the group consisting of —O—, —S—, —N($R_6$)—, and —C($R_{16}$)($R_{17}$)— wherein $R_{16}$ and $R_{17}$ are independently the same or different and are selected from the group consisting of hydrogen or a substituted or unsubstituted, saturated or unsaturated alkyl;

wherein a linker is a traceless linker selected from the group consisting of —$C_6H_4$—$CH_2$— and —$C_6H_4$—$CH_2$—$X_1$—C(=$X_2$)— wherein $X_1$ and $X_2$ are independently the same or different and are selected from the group consisting of —O—, —S— and —N($R_a$), and where $R_a$ is hydrogen or a lower alkyl; and —(CH$_2$)$_n$—NR$_b$—(C=O)— wherein n=2 or 3 and $R_b$ is hydrogen or a lower alkyl;

and wherein a toxin is an agent that is toxic upon cleavage by an activating enzyme with the proviso that the toxin is not 5-fluorodeoxyuridine, or any derivative or analog thereof.

2. A compound having the structure:

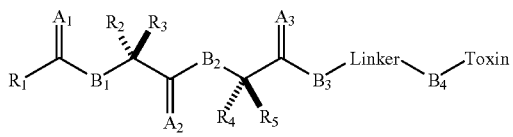

wherein $R_1$ and $R_2$ are each hydrogen and $R_4$, and $R_5$ are independently the same or different and are selected from the group consisting of hydrogen, a substituted or unsubstituted $C_5$–$C_{14}$ aryl group and a substituted or unsubstituted, saturated or unsaturated $C_1$–$C_6$ alkyl group;

wherein $R_3$ is selected from the group consisting of a substituted or unsubstituted aryl group and a substituted or unsubstituted, saturated or unsaturated $C_1$–$C_6$ alkyl group and —$CH_2$—$CH_2$—X—$CH_3$, wherein X is selected from the group consisting of —O—, —S—, —NH—, —NR$_6$—, and —$CH_2$—; where $R_6$ is a lower alkyl;

wherein $A_1$ and $A_3$ are independently the same or different and are selected from the group consisting of =O, =S, =NH, =N—OH, or =N—$R_7$, where $R_7$ is hydrogen or a $C_1$–$C_6$ alkyl;

wherein $A_2$, is absent or selected from the group consisting of =O, =S; =NH, =N—OH, =N—$R_8$, or —C($R_9$)($R_{10}$)—, wherein $R_8$, $R_9$, and $R_{10}$ are independently the same or different and are selected from the group consisting of hydrogen or a $C_1$–$C_6$ alkyl;

wherein $B_1$, is selected from the group consisting of —O—, —S—, —NH— or —N($R_{11}$)—, wherein $R_{11}$ is selected from the group consisting of hydrogen and a $C_1$–$C_6$ alkyl;

wherein $B_2$ is absent or is selected from the group consisting of —O—, —S—, —N($R_{12}$)—, or —C($R_{13}$)($R_{14}$)—, where $R_{12}$, $R_{13}$, and $R_{14}$ are independently the same or different and are selected from the group consisting of hydrogen or a substituted or unsubstituted, saturated or unsaturated alkyl;

wherein the fragment —$B_2$—C($R_4$)($R_5$)—C(=$A_3$)— in its entirety is an naturally occurring amino acid, analog, derivative or peptidomimetic thereof;

wherein $B_3$ is absent or is selected from the group consisting of —O—, —S—, or —NH—, or —N($R_{15}$)—, wherein $R_{15}$ is selected from the group consisting of hydrogen and a $C_1$–$C_6$ alkyl;

wherein $B_4$ is absent or is selected from the group consisting of —O—, —S—, —N($R_6$)—, and —C($R_{16}$)($R_{17}$)— and wherein $R_{16}$ and $R_{17}$ are independently the same or different and are selected from the group consisting of hydrogen or a substituted or unsubstituted, saturated or unsaturated alkyl;

wherein a linker is absent so that the toxin is covalently bonded to $B_3$ or $B_4$;

and wherein the toxin has the structure:

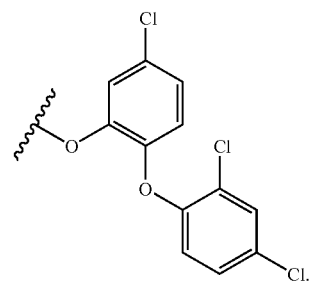

3. The compound of claim 1 or 2, wherein $R_3$ is —$CH_2$—$CH_2$—X—$CH_3$, wherein X is selected from the group consisting of oxygen, sulfur or methyl.

4. The compound of claim 3, wherein X is sulfur or oxygen.

5. The compound of claim 4, wherein $A_1$ and $A_2$ are both oxygen.

6. The compound of claim 5, wherein $B_1$ is —NH.

7. A compound of claim 2, wherein the compound has the structure:

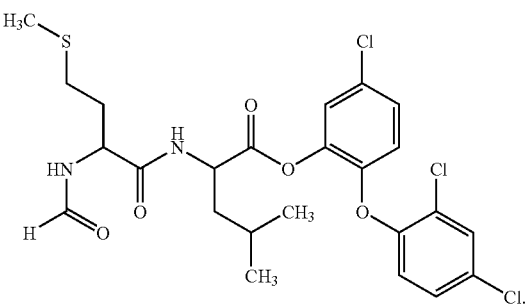

8. The compound of claim 1, wherein $B_4$ is absent.

9. The compound of claim 8, wherein the toxin is selected from the group consisting of 2-mercaptopyridine-N-oxide, ciprofloxacin, norfloxacin, nitrogen mustard and the derivatives, analogues and pharmaceutically acceptable salts thereof.

10. The compound of claim 9, wherein $B_2$ is —NH, $B_3$ is —O—, $R_4$ is 2-methyl-propyl and $R_5$ is hydrogen.

11. The compound of claim 9, wherein the toxin is norfloxacin or a derivative, analog or pharmaceutically acceptable salt thereof.

12. The compound of claim 11, wherein the fragment —$B_2$—C($R_4$)($R_5$)—C(=$A_3$)— is proline, analog, derivative or peptidomimetic thereof.

13. A compound of claim 1, wherein the compound has the structure:
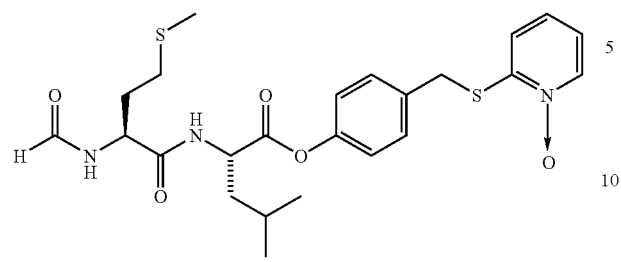
14. A compound of claim 1, wherein the compound has the structure:
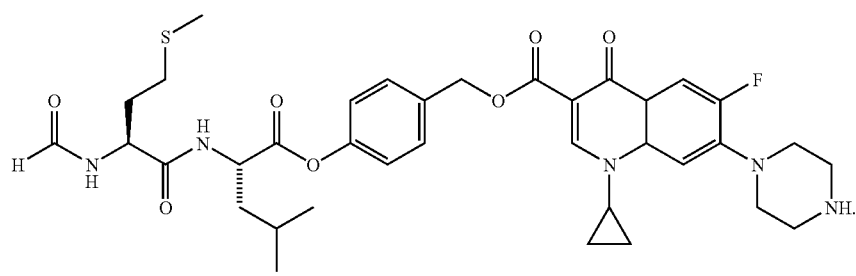
15. A compound of claim 1, wherein the compound has the structure:
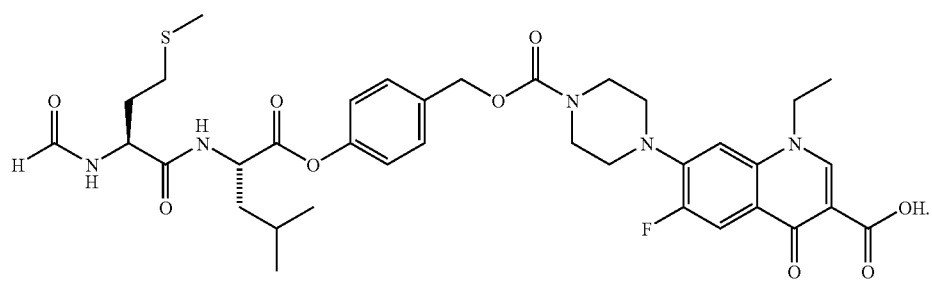
16. A compound of claim 1, wherein the compound has the structure:
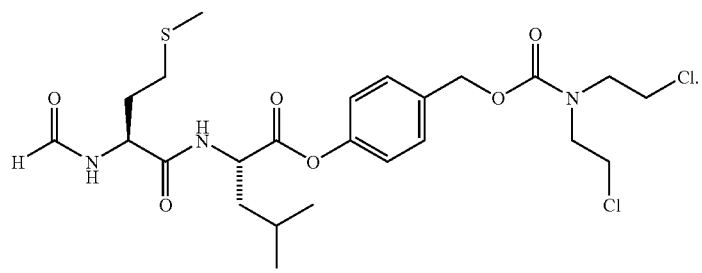
17. A compound having the structure:
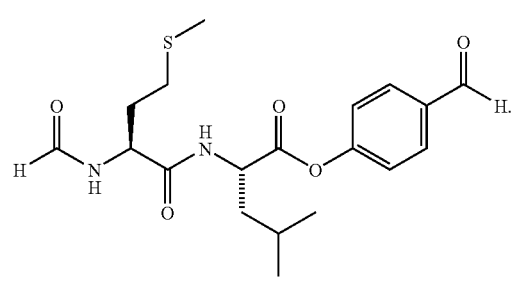

18. A compound having the structure:

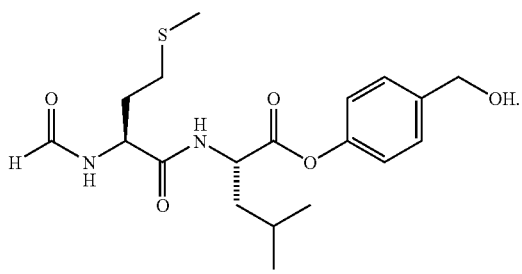

19. A composition comprising the compound of claim 1 or 2 and a carrier.

20. The composition of claim 19, wherein the carrier is a pharmaceutically acceptable carrier.

21. A method for inhibiting the growth of a microorganism that expresses peptide deformylase, comprising contacting the microorganism with an effective amount of the compound of claim 1 or 2.

22. A method for treating a subject infected with a microorganism that expresses peptide deformylase, comprising administering to the subject an effective amount of the compound of claim 1 or 2.

23. A method for identifying potential therapeutic agents that inhibit the growth of a microorganism expressing peptide deformylase, comprising
  (a) contacting a first sample of the microorganism with the potential therapeutic agent,
  (b) contacting a second sample of the microorganism with a compound of claims 1 or 2, the contacting steps (a) and (b) being performed under conditions that favor the incorporation of the potential therapeutic agent or compound into the microorganism,
  (c) assaying said first and second samples for inhibition of growth of the microorganism,
  (d) comparing the ability of the potential therapeutic agent to inhibit growth of the microorganism from said first sample with the inhibition of growth from said second sample; and
  (e) selecting those potential therapeutic agents from said first sample assay which inhibited the growth of the microorganism.

* * * * *